(12) United States Patent
Miller et al.

(10) Patent No.: US 7,407,649 B2
(45) Date of Patent: Aug. 5, 2008

(54) SILICON COMPOUNDS AND THEIR USE

(75) Inventors: David John Miller, Cambridge (GB); Parminder Kaur Ruprah, Cambridge (GB); Graham Andrew Showell, Cambridge (GB); Louise Marie Walsh, Cambridge (GB)

(73) Assignee: Paradigm Therapeutics Ltd, Cambridge (GB)

( * ) Notice: Subject to any disclaimer, the term of this patent is extended or adjusted under 35 U.S.C. 154(b) by 198 days.

(21) Appl. No.: 10/563,203

(22) PCT Filed: Jun. 18, 2004

(86) PCT No.: PCT/GB2004/002606

§ 371 (c)(1),
(2), (4) Date: Jan. 3, 2006

(87) PCT Pub. No.: WO2005/005442

PCT Pub. Date: Jan. 20, 2005

(65) Prior Publication Data

US 2007/0110708 A1    May 17, 2007

(30) Foreign Application Priority Data

Jul. 10, 2003  (GB) ................................. 0316204.7
May 14, 2004  (GB) ................................. 0410831.2

(51) Int. Cl.
*A61K 7/06* (2006.01)
*A61K 7/11* (2006.01)

(52) U.S. Cl. ..................................... 424/70.17; 528/25

(58) Field of Classification Search .............. 424/70.17; 528/25; 514/231.5, 461, 370, 336, 444, 255.05
See application file for complete search history.

(56) References Cited

U.S. PATENT DOCUMENTS 7,101,878 B1 * 9/2006 Anderson et al. ........ 514/231.5

FOREIGN PATENT DOCUMENTS

WO       WO 00/20358       4/2000

* cited by examiner

*Primary Examiner*—Yvonne Eyler
*Assistant Examiner*—Chukwuma O Nwaonicha
(74) *Attorney, Agent, or Firm*—Saliwanchik, Lloyd & Saliwanchik

(57) ABSTRACT

A compound of formula (I) or formula (II) wherein the variables are as defined in the claims

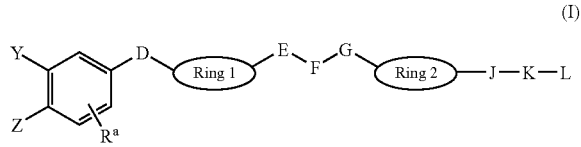

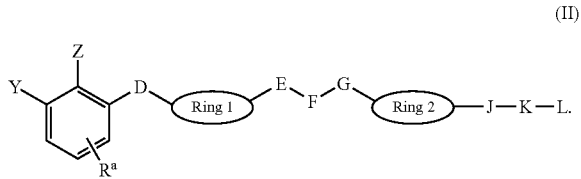

21 Claims, No Drawings

SILICON COMPOUNDS AND THEIR USE

This application is a National Stage Application of International Application Number PCT/GB2004/002606, filed Jun. 18, 2004; which claims priority to British Application Nos. 0316204.7, filed Jul. 10, 2003, and 0410831.2, filed May 14, 2004.

FIELD OF THE INVENTION

This invention relates to compounds and their use in therapy.

BACKGROUND TO THE INVENTION

Gonadotropin-Releasing Hormone (GnRH) plays a key role in the biology of reproduction. GnRH is also known as luteinizing hormone-releasing hormone (LH-RH).

The GnRH decapeptide (pyro-Glu-His-Trp-Ser-Tyr-Gly-Leu-Art-Pro-Gly-$NH_2$ or p-EHWSYGLRPG-$NH_2$) is formed in neurons of the medial basal hypothalamus from a larger precursor via enzymatic processing. The peptide is released in a pulsatile manner into the pituitary portal circulation system, where GnRH interacts with high-affinity receptors (7-transmembrane G-protein coupled receptors) in the anterior pituitary gland located at the base of the brain. Here, GnRH triggers the release of luteinizing hormone (LH) and follicle-stimulating hormone (FSH), both of which are gonadotropic hormones (gonadotropins). LH stimulates the production of testosterone and estradiol in the testes and ovaries respectively, whilst FSH stimulates follicle growth in women and sperm formation in men. When correctly functioning, the pulsatile release and concentration levels of GnRH are critical for the maintaining of gonadal steroidogenesis and for normal functions of reproduction related to growth and sexual development.

The pituitary response to GnRH varies greatly throughout life. GnRH and the gonadotropins first appear in the foetus at about ten weeks of gestation. Sensitivity to GnRH reduces until the onset of puberty. There is, however, a brief rise during the first three months after birth. Prior to puberty, the FSH response to GnRH is greater than that of LH. Once puberty begins, sensitivity to GnRH increases, and pulsatile LH secretion ensues. Later in puberty and throughout the reproductive years, pulsatile release of GnRH occurs throughout the day, with responsiveness to LH being greater than that of FSH. Pulsatile GnRH release results in pulsatile LH and FSH release and thus testosterone and estradiol release from the gonads. Post-menopause, the concentration of FSH an LH rise, and the post-menopausal levels of FSH are higher than those of LH.

Chronic administration of GnRH agonists and antagonists results in decreased circulating levels of both LH and FSH. GnRH agonists are compounds that mimic endogenous GnRH to stimulate receptors on the pituitary gland, resulting in release of LH and FSH. After a transient rise in gonadal hormone production ("flare" response), the chronic administration of GnRH agonists results in down-regulation of the GnRH receptors. This down-regulation and desensitization results in a reduction in the circulating levels of LH and FSH. In spite of the symptom-exacerbating hormonal flare experienced, GnRH agonists have been the preferred treatment for sex-steroid-dependent pathophysiologies. GnRH agonists have been used to reduce testosterone production, thereby reducing prostate volume in benign prostatic hyperplasia (BPH) and slowing tumour growth in prostate cancer. Such compounds have also been used in the treatment of breast and ovarian cancers.

In recent years, GnRH antagonists have become available for clinical evaluation, and have been shown to have an immediate effect on the pituitary but without the observed flare associated with agonists. Use of GnRH antagonists has been reported for the treatment of ovarian, breast and prostate cancers.

Other uses of antagonists include endometriosis (including endometriosis with pain), uterine myoma, ovarian and mammary cystic diseases (including polycystic ovarian disease), prostatic hypertrophy, amenorrhea (e.g. secondary amenorrhea), and precocious puberty. These compounds may also be useful in the symptomatic relief of premenstrual syndrome (PMS). Antagonists may also be useful to regulate the secretion of gonadotropins in male mammals to arrest spermatogenesis (e.g. as male contraceptives), and for treatment of male sex offenders. GnRH antagonists and agonists have been shown to have utility in treatments where a reversible suppression of the pituitary-gonadal axis is desired.

The presence of GnRH receptors on anterior pituitary cells and several tumour cell types offers the opportunity to develop drugs that act upon receptors to treat both hormone-dependent and hormone-independent cancers.

Conventionally, androgen deprivation has been the most effective systematic therapy for the treatment of metastatic carcinoma of the prostate. The prostate gland requires androgens for normal growth, maintenance, and function. Prostate cancer and benign prostate hyperplasia, however, are common in men and develop in an environment of continuous exposure to androgen. Utilizing a GnRH antagonist to interrupt the pituitary-gonadal axis reduces androgen production and results in tumour growth modulation.

GnRH antagonists may have a direct effect on tumour growth by blocking receptors on the tumour cells. For those cancer types that respond both to sex hormones and to GnRH directly, antagonists should be effective in slowing tumour growth by two mechanisms. Since GnRH receptors are present on many prostate and breast cancer cells, it has recently been proposed that GnRH antagonists may also be effective in treating non-hormone-dependent tumours. Recent literature examples indicate that GnRH receptors are present on a number of cancer cell lines. In particular, prostate, ovarian and breast cancers (see for example Montagnani et al., *Arch. Ital, Urol. Androl.* 1997, 69(4), 257-263; Jungwirth et al., *Prostate* 1997, 32(3), 164-172; Srkalovic et al., *Int. J. Oncol.* 1998, 12(3), 489-498; Kottler et al., *Int. J. Cancer* 1997, 71(4), 595-599.

Available GnRH antagonists have primarily been peptide analogues of GnRH (see, for example, WO93/03058). Peptide antagonists of peptide hormones have some potency but, the use of current peptide antagonists is often associated with problems because peptides are degraded by physiological enzymes and often poorly distributed within the organism being treated. They thus have a limited effectiveness as drugs.

WO00/20358 discloses non-peptide analogues of GnRH.

Sila-substitution (C/Si-exchange) of drugs is a relatively recent approach for searching for organo-silicon compounds which have beneficial biological properties. The approach involves the replacement of specific carbon atoms in compounds by silicon, and monitoring how the biological properties of the compounds have changed. A review of this approach is provided in Tacke and Zilch, Endeavour, New Series, 10, 191-197 (1986).

SUMMARY OF THE INVENTION

A first aspect of the invention is a compound of formula (I) or formula (II):

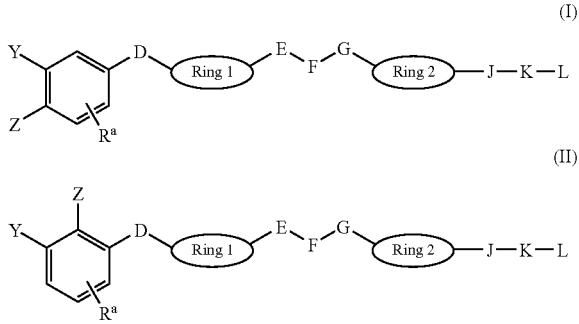

wherein

D is —(CH$_2$)$_n$—, —C(=X)—, —O—, —S(O)$_m$—, —C(=X)N(R$^e$)—, —C(R$^b$)$_2$—, —C(R$^b$)=C(R$^b$)—, —CH(R$^b$)CH(R$^b$)—;

E is optionally present and is —(CH$_2$)$_n$—, —N(R$^d$)— or —N(R$^d$)(CH$_2$)$_n$—;

F is —C(=X)— or —N(R$^d$)—;

G is —(CH$_2$)$_n$—, —N(R$^d$)—, —(CH$_2$)$_n$N(R$^d$)— or —N(R$^d$)(CH$_2$)$_n$;

J is optionally present and is —O—, —N(R$^e$)C(=X)N(R$^e$)—, —S(O)$_m$—, —N(R$^e$)S(O)$_m$—, —S(O)$_m$N(R$^e$)— or —N(R$^e$)—;

K is optionally present and is alkylene optionally substituted with R$^b$; or K is cycloalkylene, cycloalkenylene, arylene, heterocycloalkylene, heterocycloalkylene or heteroarylene, any of which is optionally substituted with R$^a$;

L is hydrogen, halogen, —N(R$^f$)$_2$, cycloalkyl, cycloalkenyl, aryl, heterocycloalkyl, heterocycloalkenyl or heteroaryl, any of which is optionally substituted with R$^a$, —C(=X)OR$^d$, —OH, —OR$^c$, —C(=X)N(R$^b$)(R$^c$) or —CN;

each R$^a$ is the same or different and is hydrogen, halogen, alkyl, aryl, hydroxy, alkoxy, -alkoxy-(CH$_2$)$_n$C(O)$_2$R$^b$, —O-aryl, —C(=X)R$^c$, —NO$_2$, —CN, —N(R$^c$)C(=X)R$^c$, —C(=X)N(R$^e$)$_2$, —S(O)$_2$N(R$^e$)$_2$ or —N(R$^e$)$_2$;

each R$^b$ is the same or different and is hydrogen or alkyl;

each R$^c$ is the same or different and is alkyl, cycloalkyl, -alkyl-aryl, -alkyl-cycloalkyl or aryl optionally substituted with R$^a$;

each R$^d$ is the same or different and is hydrogen, alkyl or aryl optionally with R$^a$;

each R$^e$ is the same or different and is hydrogen, alkyl; or R$^e$ is aryl or heteroaryl, either of which is optionally substituted with R$^a$;

each R$^f$ is the same or different and is hydrogen or alkyl; or R$^f$—N—R$^f$ taken together form heterocycloalkyl, heterocycloalkenyl or heteroaryl;

each X is the same or different and is oxygen or sulphur;

Y and Z are the same or different and are each hydrogen, halogen, alkyl, hydroxy, alkoxy, —CN, —N(R$^d$)C(=X)R$^c$, —C(=X)N(R$^c$)(R$^d$), —S(O)$_m$—R$^c$, —N(R$^c$)(R$^d$)S(O)$_2$, —S(O)$_2$N(R$^c$)(R$^d$), —N(R$^e$)$_2$, —Si(R$^c$)$_3$, -alkyl-Si(R$^c$)$_3$, aryl optionally substituted with R$^a$ or —O-aryl optionally substituted with R$^a$;

Rings 1 and 2 are the same or different and are each arylene or heteroarylene, either of which is optionally substituted with R$^a$;

each m is the same or different and is 0, 1 or 2; and each n is the same or different and is 0, 1, 2, or 3;

with the provisos that at least one of Y and Z comprises a silicon atom and that the compound does not contain a N—N single bond;

or a pharmaceutically acceptable salt thereof.

Compounds of the invention may act as GnRH antagonists and, as a result, may have utility in cancer therapy or in the treatment or prevention of endometriosis, uterine myoma, an ovarian disease, a mammary cystic disease, prostatic hypertrophy, amenorrhea, precocious puberty, premenstrual syndrome, a sex-steroid-dependent pathophysiology, benign prostatic hyperplasia, Alzheimer's disease, HIV infection, AIDS or a disease caused by thyroid malfunction, or to arrest spermatogenesis.

Accordingly, a second aspect of the invention is the use of a compound of the invention for the manufacture of a medicament for cancer therapy or for the treatment or prevention of endometriosis, uterine myoma, an ovarian disease, a mammary cystic disease, prostatic hypertrophy, amenorrhea, precocious puberty, premenstrual syndrome, a sex-steroid-dependent pathophysiology, benign prostatic hyperplasia, Alzheimer's disease, HIV infection, AIDS or a disease caused by thyroid malfunction, or to arrest spermatogenesis.

Another aspect of the invention is a pharmaceutical composition comprising a compound of the invention and a pharmaceutically acceptable diluent or carrier.

DESCRIPTION OF THE INVENTION

Certain compounds and combinations of substituents are preferred; in particular see the subclaims.

The term "alkyl" as used herein refers to an optionally substituted straight or branched chain alkyl moiety having from one to six carbon atoms. The term includes, for example, methyl, ethyl, propyl, isopropyl, butyl, tert-butyl, pentyl, hexyl and the like. The substituents may be the same or different in each occurrence and selected from halogen and the like. "C$_{1-6}$ alkyl" has the same meaning. "Alkylene" refers to a similar, divalent group.

The term "alkoxy" as used herein refers to an optionally substituted straight or branched chain alkoxy group containing one to six carbon atoms. The term includes, for example, methoxy, ethoxy, propoxy, isopropoxy, butoxy, tert-butoxy, pentoxy, hexoxy and the like. The substituents may be the same or different in each occurrence and selected from halogen and the like. "C$_{1-6}$ alkoxy" has the same meaning.

The term "halogen" as used herein refers to F, Cl, Br or I.

The term "aryl" as used herein refers to optionally substituted aromatic ring systems comprising six to ten ring atoms, and optionally substituted polycyclic ring systems having two or more cyclic rings at least one of which is aromatic. This term includes, for example, phenyl and naphthyl. The group may be optionally substituted with the substituents being the same or different in each occurrence and selected from R$^a$ and the like. "Arylene" refers to a similar, divalent group.

The term "cycloalkyl" as used herein refers to a saturated alicyclic moiety having from three to six carbon atoms. The term includes, for example, cyclopropyl, cyclobutyl, cyclopentyl, cyclohexyl and the like. The group may be optionally substituted by any substituent described herein. "Cycloalkylene" refers to a similar, divalent group.

The term "cycloalkenyl" as used herein refers to an alicyclic moiety having from three to six carbon atoms and having in addition at least one double bond. The term includes, for example, cyclopentenyl, cyclohexenyl and the like. The group may be optionally substituted by any substituent described herein. "Cycloalkenylene" refers to a similar, divalent group.

The term "heterocycloalkyl" as used herein refers to a saturated heterocyclic moiety having from three to seven carbon atoms and one or more heteroatoms selected from the group N, O, S, P and Si. The term includes, for example, azetidinyl, pyrrolidinyl, tetrahydrofuranyl, piperidinyl and the like. The group may be optionally substituted by any substituent described herein. "Heterocycloalkylene" refers to a similar, divalent group.

The term "heteroaryl" as used herein refers to aromatic ring systems of five to ten atoms at least one atom of which is selected from O, N and S. The term includes, for example, furanyl, thiophenyl, pyridyl, indolyl, quinolyl and the like. The group may be optionally substituted with $R^a$ and the like. "Heteroarylene" refers to a similar, divalent group.

The term "heterocyclyl" as used herein refers to a saturated or unsaturated heterocyclic ring moiety having from three to seven carbon atoms and one or more heteroatoms selected from N, O, S, P and Si. The term includes, for example, piperidinyl, pyrrolidinyl, morpholinyl and the like. The group may be polycyclic (e.g. a fused ring system), the group comprising two or more rings, at least one of which comprises a heteroatom.

Preferred compounds of the invention include:

5-[2-methyl-5-(trimethylsilyl)phenoxy]-N-(2,6-dimethoxyphenyl)furan-2-carboxamide;

5-[2-methyl-5-(trimethylsilyl)phenoxy]-N-(2,4,6-trimethoxyphenyl)furan-2-carboxamide;

5-[2-methyl-5-(trimethylsilyl)phenoxy]-N-(2,4,6-trimethoxy-1,3-pyrimidin-5-yl)furan-2-carboxamide;

5-[2-methyl-5-(trimethylsilyl)phenoxy]-N-(2-methylamino-4,6-dimethoxy-1,3-pyrimidin-5-yl)furan-2-carboxamide;

5-[2-methyl-5-(trimethylsilyl)phenoxy]-N-{2-[3-(4-methylpiperazin-1-yl)propylamino]-4,6-dimethoxy-1,3-pyrimidin-5-yl}furan-2-carboxamide;

5-[2-methyl-5-(trimethylsilyl)phenoxy]-N-{2-[3-(N,N-dimethylamino)propylamino]-4,6-dimethoxy-1,3-pyrimidin-5-yl}furan-2-carboxamide;

5-[2-methyl-5-(trimethylsilyl)phenoxy]-N-{2-[3-(morpholin-4-yl)propylamino]-4,6-dimethoxy-1,3-pyrimidin-5-yl}furan-2-carboxamide;

5-[2-methyl-5-(trimethylsilyl)phenoxy]-N-{2-[2-(pyrrolidin-1-yl)ethylamino]-4,6-dimethoxy-1,3-pyrimidin-5-yl}furan-2-carboxamide;

5-[2-methyl-5-(trimethylsilyl)phenoxy]-N-{2-[3-(1,3-imidaz-1-yl)propylamino]-4,6-dimethoxy-1,3-pyrimidin-5-yl}furan-2-carboxamide;

5-[2-bromo-5-(trimethylsilyl)phenoxy]-N-(2,6-dimethoxyphenyl)furan-2-carboxamide;

5-[2-bromo-5-(trimethylsilyl)phenoxy]-N-(2,4,6-trimethoxyphenyl)furan-2-carboxamide;

5-[2-bromo-5-(trimethylsilyl)phenoxy]-N-(2,4,6-trimethoxy-1,3-pyrimidin-5-yl)furan-2-carboxamide;

5-[2-bromo-5-(trimethylsilyl)phenoxy]-N-(2-methylamino-4,6-dimethoxy-1,3-pyrimidin-5-yl)furan-2-carboxamide;

5-[2-bromo-5-(trimethylsilyl)phenoxy]-N-{2-[3-(4-methylpiperazinyl)propylamino]-4,6-dimethoxy-1,3-pyrimidin-5-yl}furan-2-carboxamide;

5-[2-bromo-5-(trimethylsilyl)phenoxy]-N-{2-[3-(N,N-dimethylamino)propylamino]-4,6-dimethoxy-1,3-pyrimidin-5-yl}furan-2-carboxamide;

5-[2-bromo-5-(trimethylsilyl)phenoxy]-N-{-2-[(3-morpholin-4-yl)propylamino]-4,6-dimethoxy-1,3-pyrimidin-5-yl}furan-2-carboxamide;

5-[2-bromo-5-(trimethylsilyl)phenoxy]-N-{2-[2-(pyrrolidin-1-yl)ethylamino]-4,6-dimethoxy-1,3-pyrimidin-5-yl}furan-2-carboxamide;

5-[2-bromo-5-(trimethylsilyl)phenoxy]-N-{2-[3-(1,3-imidaz-1-yl)propylamino]-4,6-dimethoxy-1,3-pyrimidin-5-yl}furan-2-carboxamide;

5-[2-methoxy-5-(trimethylsilyl)phenoxy]-N-(2,6-dimethoxyphenyl)furan-2-carboxamide;

5-[2-methoxy-5-(trimethylsilyl)phenoxy]-N-(2,4,6-trimethoxyphenyl)furan-2-carboxamide;

5-[2-methoxy-5-(trimethylsilyl)phenoxy]-N-(2,4,6-trimethoxy-1,3-pyrimidin-5-yl)furan-2-carboxamide;

5-[2-methoxy-5-(trimethylsilyl)phenoxy]-N-(2-methylamino-4,6-dimethoxy-1,3-pyrimidin-5-yl)furan-2-carboxamide;

5-[2-methoxy-5-(trimethylsilyl)phenoxy]-N-{2-[3-(4-methylpiperazin-1-yl)propylamino]-4,6-dimethoxy-1,3-pyrimidin-5-yl}furan-2-carboxamide;

5-[2-methoxy-5-(trimethylsilyl)phenoxy]-N-{2-[3-(N,N-dimethylamino)propylamino]-4,6-dimethoxy-1,3-pyrimidin-5-yl}furan-2-carboxamide;

5-[2-methoxy-5-(trimethylsilyl)phenoxy]-N-{2-[3-(morpholin-4-yl)propylamino]-4,6-dimethoxy-1,3-pyrimidin-5-yl}furan-2-carboxamide;

5-[5-(ethyldimethylsilyl)-2-methylphenoxy]-N-(2,6-dimethoxyphenyl)furan-2-carboxamide;

5-[5-(ethyldimethylsilyl)-2-methylphenoxy]-N-(2,4,6-trimethoxyphenyl)furan-2-carboxamide;

5-[5-(ethyldimethylsilyl)-2-methylphenoxy]-N-(2,4,6-trimethoxy-1,3-pyrimidin-5-yl)furan-2-carboxamide;

5-[5-(ethyldimethylsilyl)-2-methylphenoxy]-N-(2-methylamino-4,6-dimethoxy-1,3-pyrimidin-5-yl)furan-2-carboxamide;

5-[5-(ethyldimethylsilyl)-2-methylphenoxy]-N-{2-[3-(4-methylpiperazin-1-yl)propylamino]-4,6-dimethoxy-1,3-pyrimidin-5-yl}furan-2-carboxamide;

5-[5-(ethyldimethylsilyl)-2-methylphenoxy]-N-{2-[3-(N,N-dimethylamino)propylamino]-4,6-dimethoxy-1,3-pyrimidin-5-yl}furan-2-carboxamide;

5-[5-(ethyldimethylsilyl)-2-methylphenoxy]-N-{2-[3-(morpholin-4-yl)propylamino]-4,6-dimethoxy-1,3-pyrimidin-5-yl}furan-2-carboxamide;

5-{5-[(2,2-dimethylpropyl)dimethylsilyl]-2-methylphenoxy}-N-(2,6-dimethoxyphenyl)furan-2-carboxamide;

5-{5-[(2,2-dimethylpropyl)dimethylsilyl]-2-methylphenoxy}-N-(2,4,6-trimethoxyphenyl)furan-2-carboxamide;

5-{5-[(2,2-dimethylpropyl)dimethylsilyl]-2-methylphenoxy}-N-(2,4,6-trimethoxy-1,3-pyrimidin-5-yl)furan-2-carboxamide;

5-{5-[(2,2-dimethylpropyl)dimethylsilyl]-2-methylphenoxy}-N-(2-methylamino-4,6-dimethoxy-1,3-pyrimidin-5-yl)furan-2-carboxamide;

5-{5-[(2,2-dimethylpropyl)dimethylsilyl]-2-methylphenoxy}-N-{2-[3-(4-methylpiperazin-1-yl)propylamino]4,6-dimethoxy-1,3-pyrimidin-5-yl}furan-2-carboxamide;

5-{5-[(2,2-dimethylpropyl)dimethylsilyl]-2-methylphenoxy}-N-{2-[3-(N,N-dimethylamino)propylamino]-4,6-dimethoxy-1,3-pyrimidin-5-yl}furan-2-carboxamide;

5-{5-[(2,2-dimethylpropyl)dimethylsilyl]-2-methylphenoxy}-N-{2-[3-(morpholin-4-yl)propylamino]-4,6-dimethoxy-1,3-pyrimidin-5-yl}furan-2-carboxamide;

5-{5-[1,1-dimethyl-2-(trimethylsilyl)ethyl]-2-methylphenoxy}-N-(2,6-dimethoxyphenyl)furan-2-carboxamide;

5-{5-[1,1-dimethyl-2-(trimethylsilyl)ethyl]-2-methylphenoxy}-N-(2,4,6-trimethoxyphenyl)furan-2-carboxamide;

5-{5-[1,1-dimethyl-2-(trimethylsilyl)ethyl]-2-methylphenoxy}-N-(2,4,6-trimethoxy-1,3-pyrimidin-5-yl)furan-2-carboxamide;

5-{5-[1,1-dimethyl-2-(trimethylsilyl)ethyl-2-methylphenoxy}-N-(2-methylamino-4,6-dimethoxy-1,3-pyrimidin-5-yl)furan-2-carboxamide;

5-{5-[1,1-dimethyl-2-(trimethylsilyl)ethyl]-2-methylphenoxy}-N-{2-[3-(4-methylpiperazin-1-yl)propylamino]-4,6-dimethoxy-1,3-pyrimidin-5-yl}furan-2-carboxamide;

5-{5-[1,1-dimethyl-2-(trimethylsilyl)ethyl]-2-methylphenoxy}-N-{2-[3-(N,N-dimethylamino)propylamino]-4,6-dimethoxy-1,3-pyrimidin-5-yl}furan-2-carboxamide;

5-{5-[1,1-dimethyl-2-(trimethylsilyl)ethyl]-2-methylphenoxy}-N-{2-[3-(morpholin-4-yl)propylamino]-4,6-dimethoxy-1,3-pyrimidin-5-yl}furan-2-carboxamide;

5-{[2-methyl-5-trimethylsilyl)phenyl]methyl}-N-(2,6-dimethoxyphenyl)furan-2-carboxamide;

5-{[2-methyl-5-(trimethylsilyl)phenyl]methyl}-N-(2,4,6-trimethoxyphenyl)furan-2-carboxamide;

5-{[2-methyl-5-(trimethylsilyl)phenyl]methyl}-N-(2,4,6-trimethoxy-1,3-pyrimidin-5-yl)furan-2-carboxamide;

5-{[2-methyl-5-(trimethylsilyl)phenyl]methyl}-N-(2-methylamino-4,6-dimethoxy-1,3-pyrimidin-5-yl)furan-2-carboxamide;

5-{[2-methyl-5-(trimethylsilyl)phenyl]methyl}-N-{2-[3-(4methylpiperazin-1-yl)propylamino]-4,6-dimethoxy-1,3-pyrimidin-5-yl}furan-2-carboxamide;

5-{[2-methyl-5-(trimethylsilyl)phenyl]methyl-N-{2-[3-(N,N-dimethylamino)propylamino]-4,6-dimethoxy-1,3-pyrimidin-5-yl}furan-2-carboxamide;

5-{[2-methyl-5-(trimethylsilyl)phenyl]methyl}-N-{2-[3-(morpholin-4-yl)propylamino]-4,6-dimethoxy-1,3-pyrimidin-5-yl}furan-2-carboxamide;

5-[2-methoxy-4-phenoxy-5-(trimethylsilyl)phenylthio]-N-[4,6-dimethoxy-(2-phenylamino)-1,3-pyrimidin-5-yl]furan-2-carboxamide;

5-{2-methoxy-5-[(2,2-dimethylpropyl)dimethylsilyl]phenoxy}-N-[2-(N-tert-butyloxycarbonylpiperidinyl-4'-amino)-4,6-dimethoxy-1,3-pyrimidin-5-yl]furan-2-carboxamide;

5-{2-methoxy-5-[(2,2-dimethylpropyl)dimethylsilyl]phenoxy}-N-{2-[3-(1,3-imidaz-1-yl)propylamino]-4,6-dimethoxy-1,3-pyrimidin-5-yl}furan-2-carboxamide;

5-{[(1,1-dimethylethyl)dimethylsilyl]phenoxy}-N-(2,4,6-trimethoxyphenyl)benzene-3-carboxamide;

5-[2-methoxy-4-(dimethylphenylsilyl)phenoxy]-N-}2-[2-(ethylamino)ethylamino]-4,6-dimethoxy-1,3-pyrimidin-5-yl}furan-2-carboxamide;

5-[4-chloro-2-methyl-5-(trimethylsilyl)phenoxy]-N-(2,4,6-trimethoxy-1,3-pyrimidin-5-yl)furan-2-carboxamide;

5-[4-chloro-2-methoxy-6-methyl-3-(trimethylsilyl)phenoxy]-N-{2-[3-(4-methylpiperazin-1-yl)propylamino]-4,6-dimethoxy-1,3-pyrimidin-5-yl}furan-2-carboxamide;

5-[2-methyl-5-(propyldimethylsilyl)phenoxy]-N-(2,4,6-trimethoxyphenyl)furan-2-carboxamide;

5-[2-methyl-5-(trimethylsilyl)phenoxy]-N-[2-(N-tert-butyloxycarbonylpiperidinyl-4'-amino)-4,6-dimethoxy-1,3-pyrimidin-5-yl]furan-2-carboxamide;

5-[2-methoxy-5-(trimethylsilyl)phenoxy]-N-[2-(3-methoxycarbonylpropylamino)-4,6-dimethoxy-1,3-pyrimidin-5-yl]furan-2-carboxamide;

5-[2-bromo-5-(trimethylsilyl)phenoxy]-N-{[2-(2-(propylamino)ethylamino]-4,6-dimethoxy-1,3-pyrimidin-5-yl}furan-2-carboxamide;

5-[2-bromo-5-(trimethylsilyl)phenoxy]-N-{2-[(2-aminoethyl)propylamino)]-4,6-dimethoxy-1,3-pyrimidin-5-yl}furan-2-carboxamide;

5-[2-bromo-5-(trimethylsilyl)phenoxy]-N-(2-chloro-4,6-dimethoxy-1,3-pyrimidin-5-yl)furan-2-carboxamide;

5-{2-methyl-4-[(2,2-dimethylpropyl)dimethylsilyl]phenoxy}-N-(2,4,6-trimethoxyphenyl)furan-2-carboxamide;

5-{2-methyl-4-[1,1-dimethyl-2-(trimethylsilyl)ethyl]phenoxy}-N-(2,4,6-trimethoxyphenyl)furan-2-carboxamide;

5-[2-methyl-4,5-bis(trimethylsilyl)phenoxy]-N-(2,4,6-trimethoxyphenyl)furan-2-carboxamide;

5-[2-methyl-4-(trimethylsilyl)phenoxy]-N-(2,6-dimethoxyphenyl)furan-2-carboxamide;

5-[2-methyl-4-(trimethylsilyl)phenoxy]-N-(2,4,6-trimethoxyphenyl)furan-2-carboxamide;

5-[2-methyl-4-(trimethylsilyl)phenoxy]-N-(2,4,6-trimethoxy-1,3-pyrimidin-5-yl)furan-2-carboxamide;

5-[2-methyl-4-(trimethylsilyl)phenoxy]-N-(2-methylamino-4,6-dimethoxy-1,3-pyrimidin-5-yl)furan-2-carboxamide;

5-[2-methyl-4-(trimethylsilyl)phenoxy]-N-{2-[3-(4-methylpiperazin-1-yl)propylamino]-4,6-dimethoxy-1,3-pyrimidin-5-yl}furan-2-carboxamide;

5-[2-methyl-4-(trimethylsilyl)phenoxy]-N-{2-[3-(N,N-dimethylamino)propylamino]-4,6-dimethoxy-1,3-pyrimidin-5-yl}furan-2-carboxamide;

5-[2-methyl-4-(trimethylsilyl)phenoxy]-N-{2-[3-(morpholin-4-yl)propylamino]-4,6-dimethoxy-1,3-pyrimidin-5-yl}furan-2-carboxamide;

5-[2-methyl-4-(trimethylsilyl)phenoxy]-N-{2-[2-(pyrrolidin-1-yl)ethylamino]-4,6-dimethoxy-1,3-pyrimidin-5-yl}furan-2-carboxamide;

5-[2-methyl-4-(trimethylsilyl)phenoxy]-N-{2-[3-(1,3-imidaz-1-yl)propylamino]-4,6-dimethoxy-1,3-pyrimidin-5-yl}furan-2-carboxamide;

5-[2-chloro-5-(trimethylsilyl)phenoxy]-N-(2,6-dimethoxyphenyl)furan-2-carboxamide;

5-[2-chloro-5-(trimethylsilyl)phenoxy]-N-(2,4,6-trimethoxyphenyl)furan-2-carboxamide;

5-[2-chloro-5-(trimethylsilyl)phenoxy]-N-(2,4,6-trimethoxy-1,3-pyrimidin-5-yl)furan-2-carboxamide;

5-[2-chloro-5-(trimethylsilyl)phenoxy]-N-(2-methylamino4,6-dimethoxy-1,3-pyrimidin-5-yl)furan-2-carboxamide;

5-[2-chloro-5-(trimethylsilyl)phenoxy]-N-{2-[3-(4-methylpiperazin-1-yl)propylamino]-4,6-dimethoxy-1,3-pyrimidin-5-yl}furan-2-carboxamide;

5-[2-chloro-5-(trimethylsilyl)phenoxy]-N-{2-[3-(N,N-dimethylamino)propylamino]-4,6-dimethoxy-1,3-pyrimidin-5-yl}furan-2-carboxamide;

5-[2-chloro-5-(trimethylsilyl)phenoxy]-N-{2-[3-(morpholin-4-yl)propylamino]-4,6-dimethoxy-1,3-pyrimidin-5-yl}furan-2-carboxamide;

5-[2-chloro-5-(trimethylsilyl)phenoxy]-N-{2-[2-(pyrrolidin-1-yl)ethylamino]-4,6-dimethoxy-1,3-pyrimidin-5-yl}furan-2-carboxamide;

5-[2-chloro-5-(trimethylsilyl)phenoxy]-N-{2-[3-(1,3-imidaz-1-yl)propylamino]-4,6-dimethoxy-1,3-pyrimidin-5-yl}furan-2-carboxamide;

the corresponding structures of which are shown below, respectively (ordered left to right):

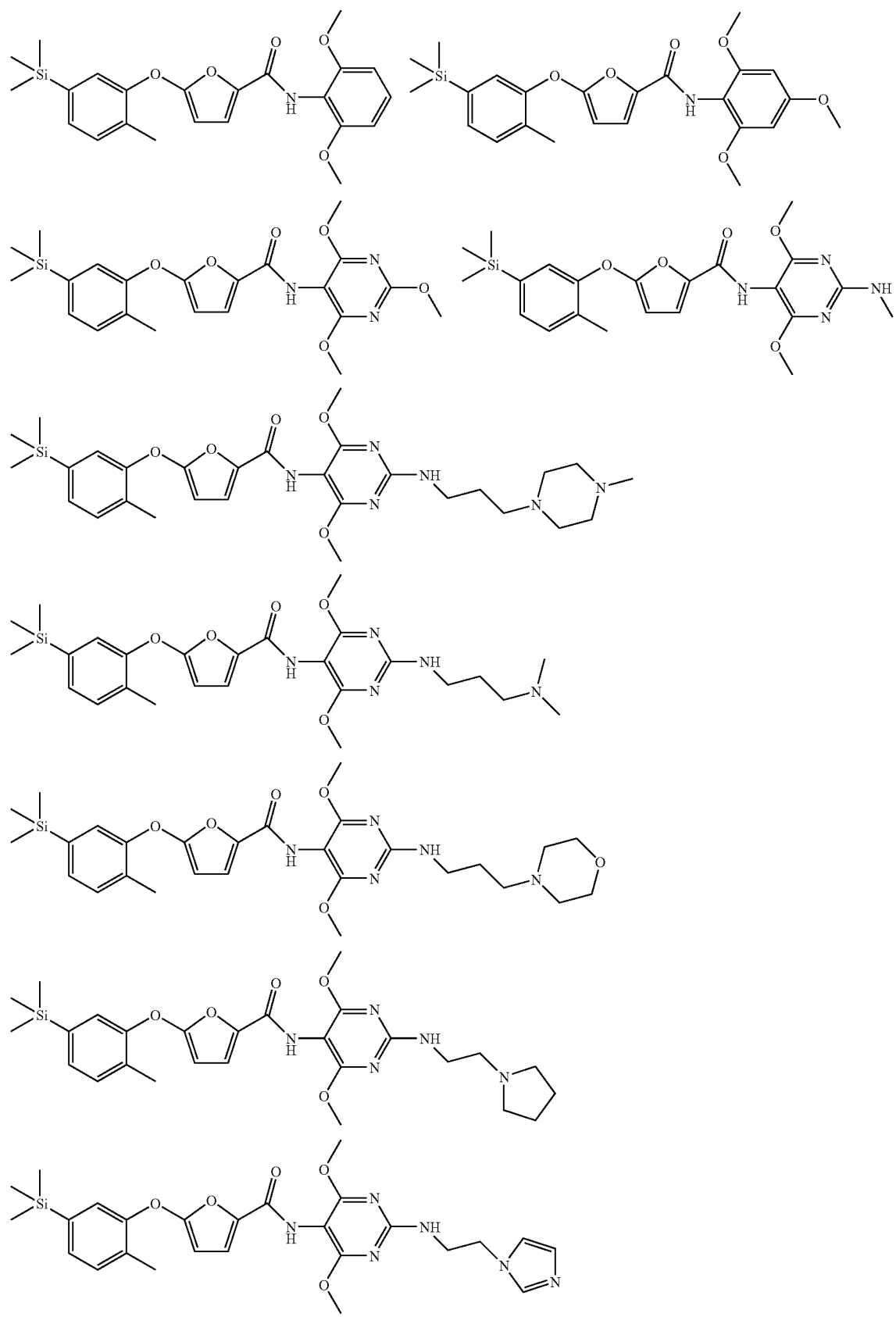

-continued
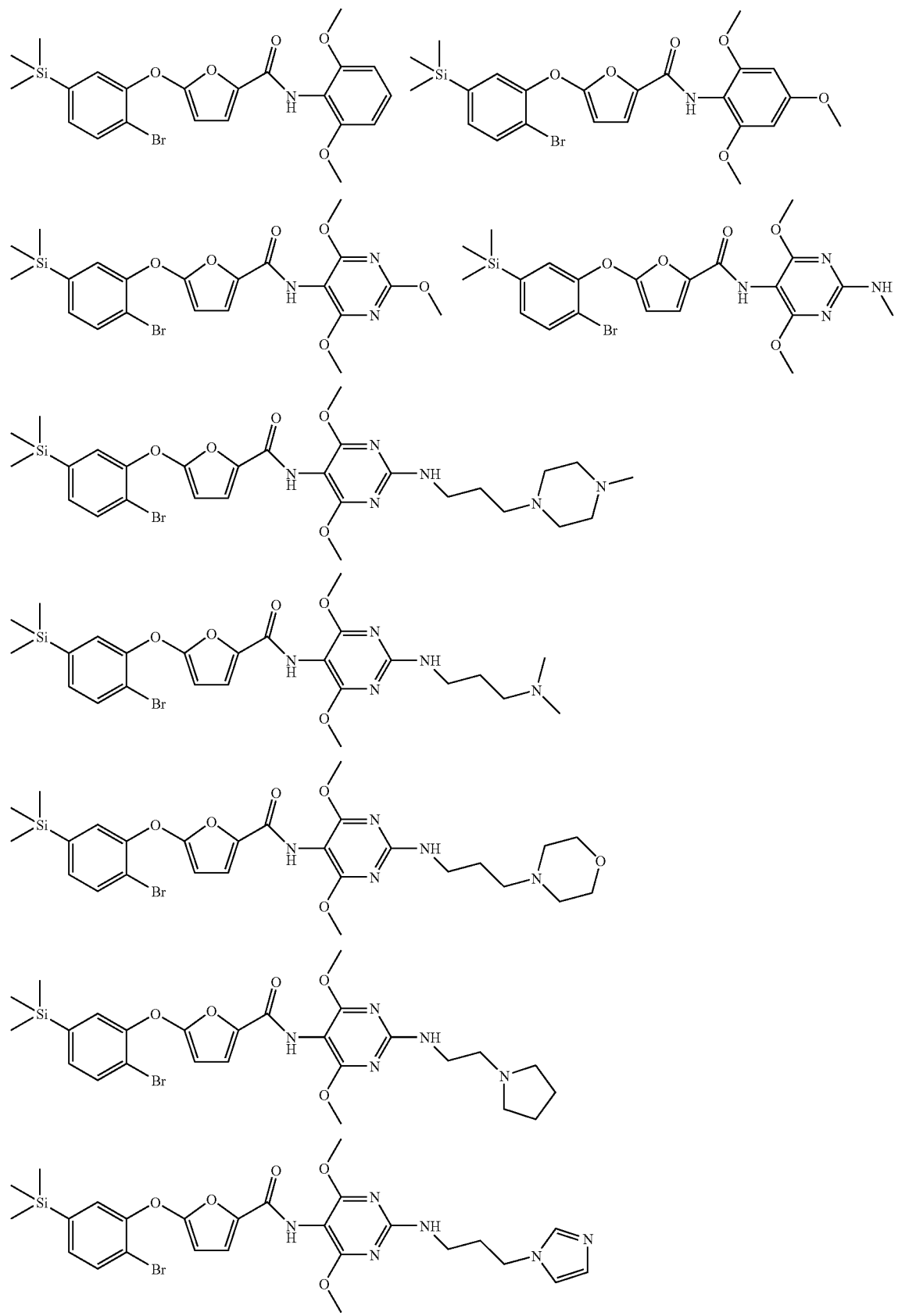

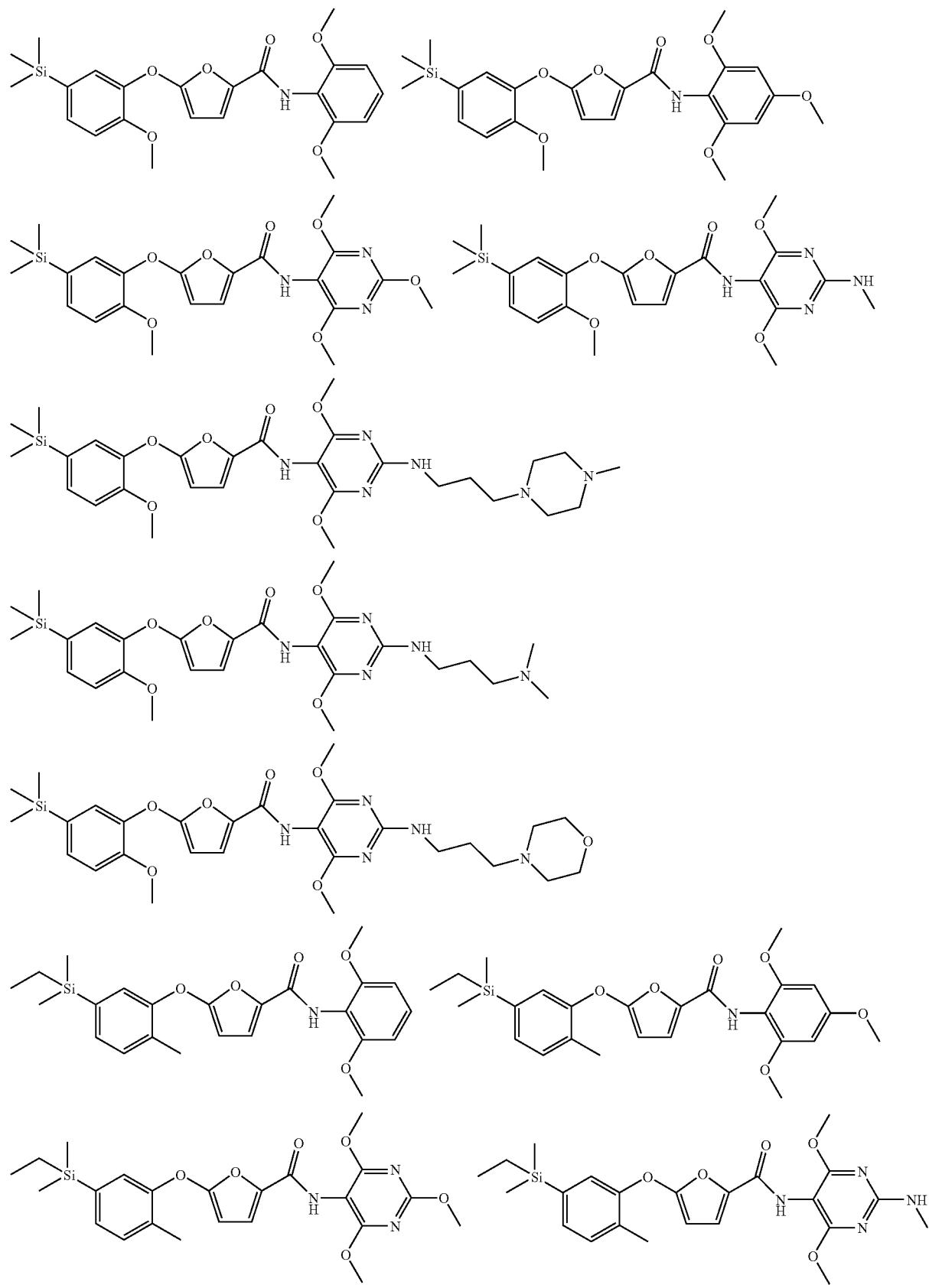

-continued
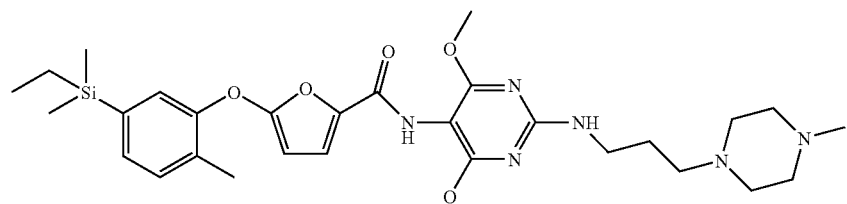
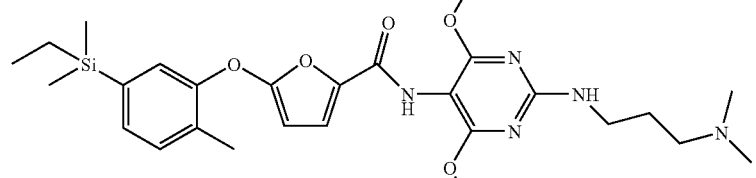
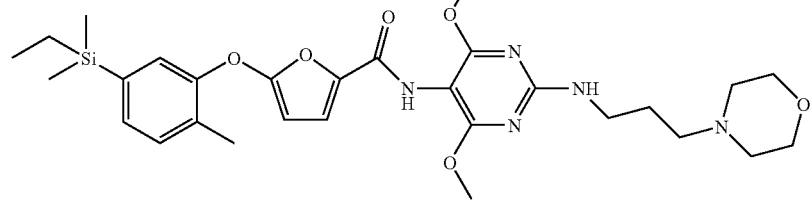
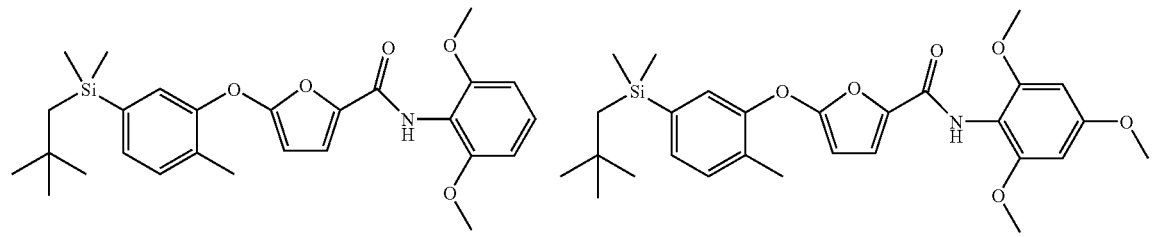
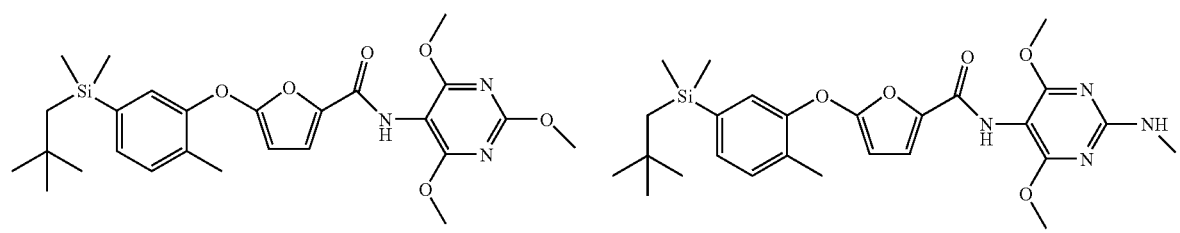
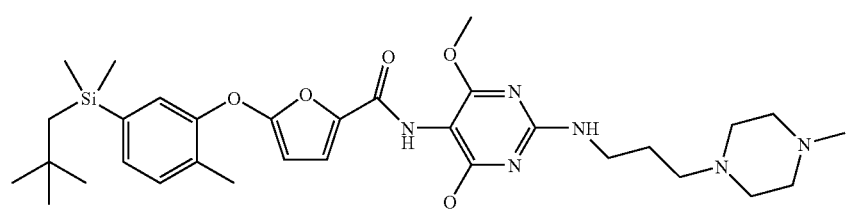
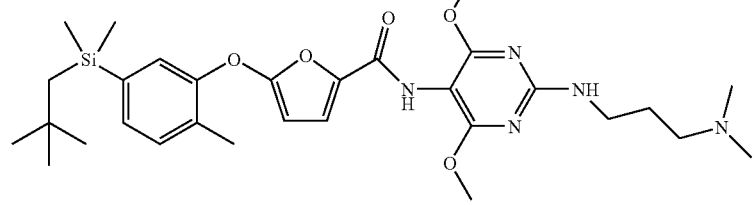

-continued
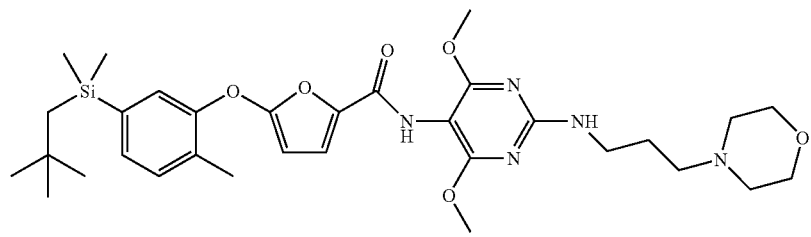
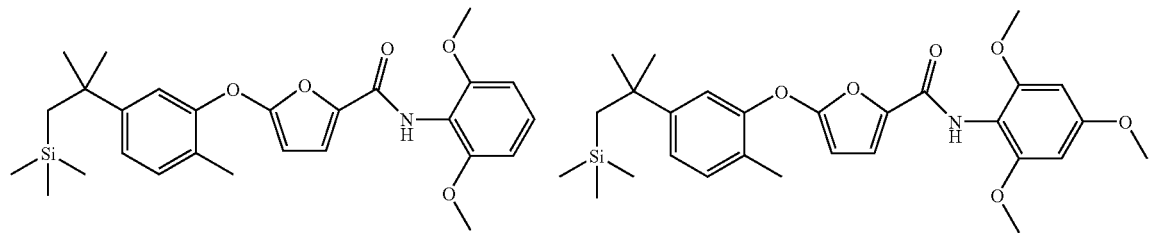
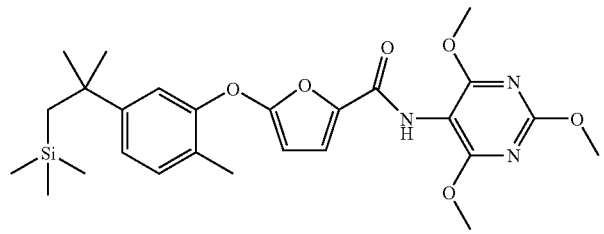
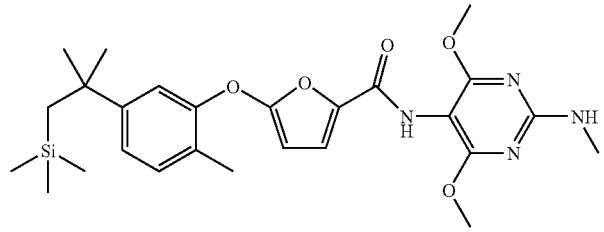
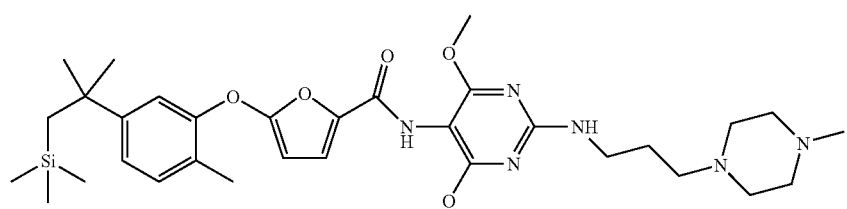
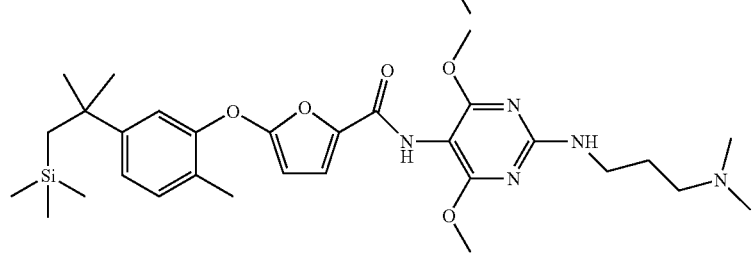
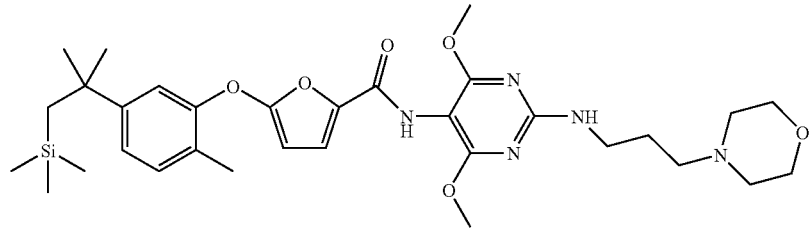

-continued
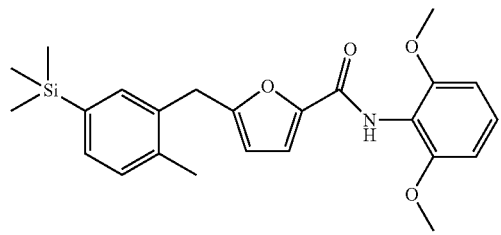
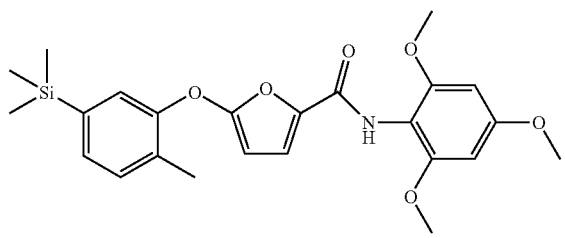
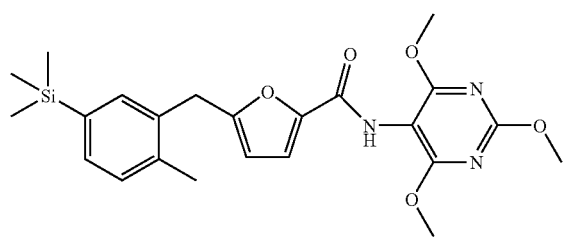
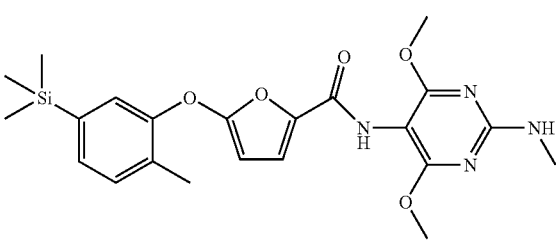
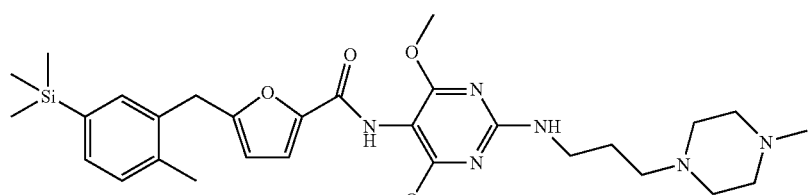
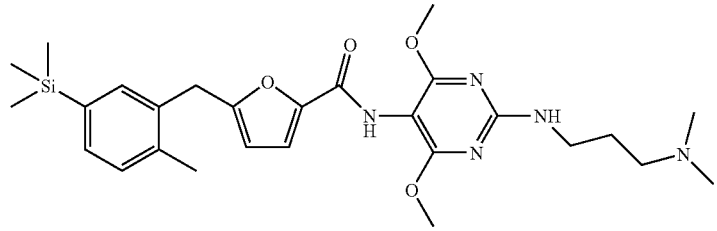
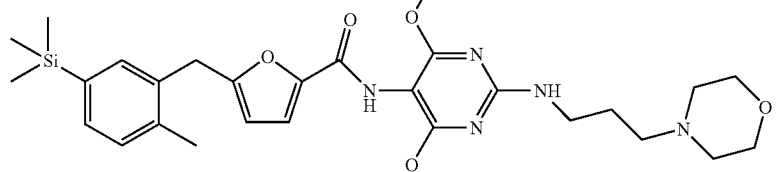
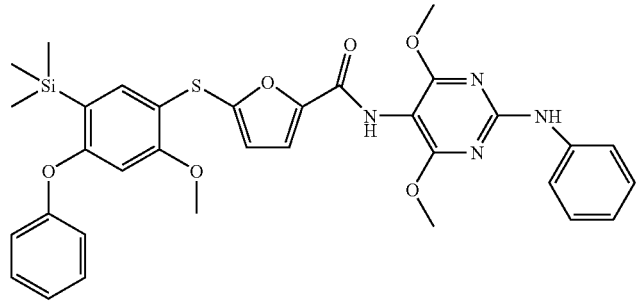

-continued
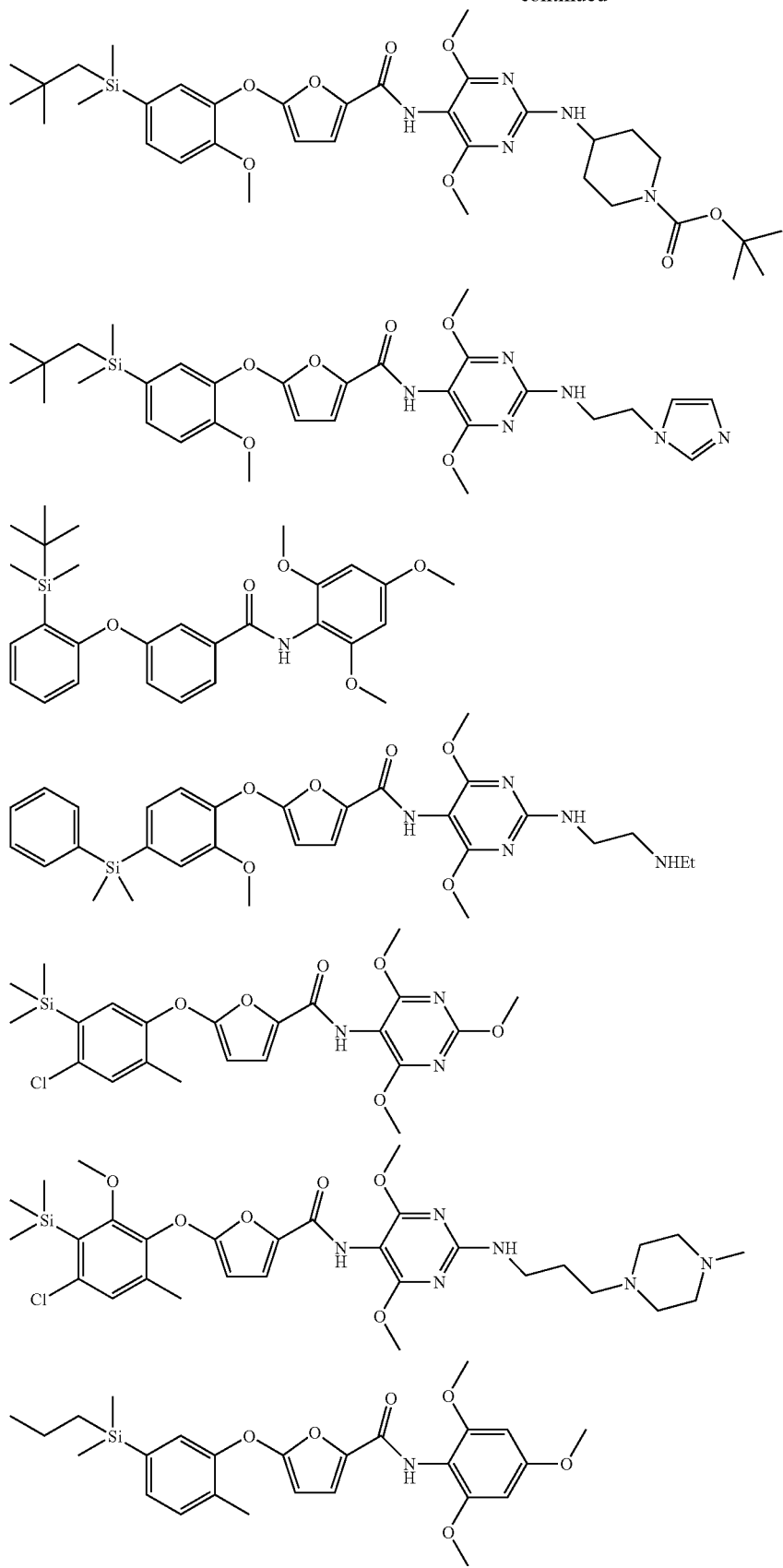

-continued
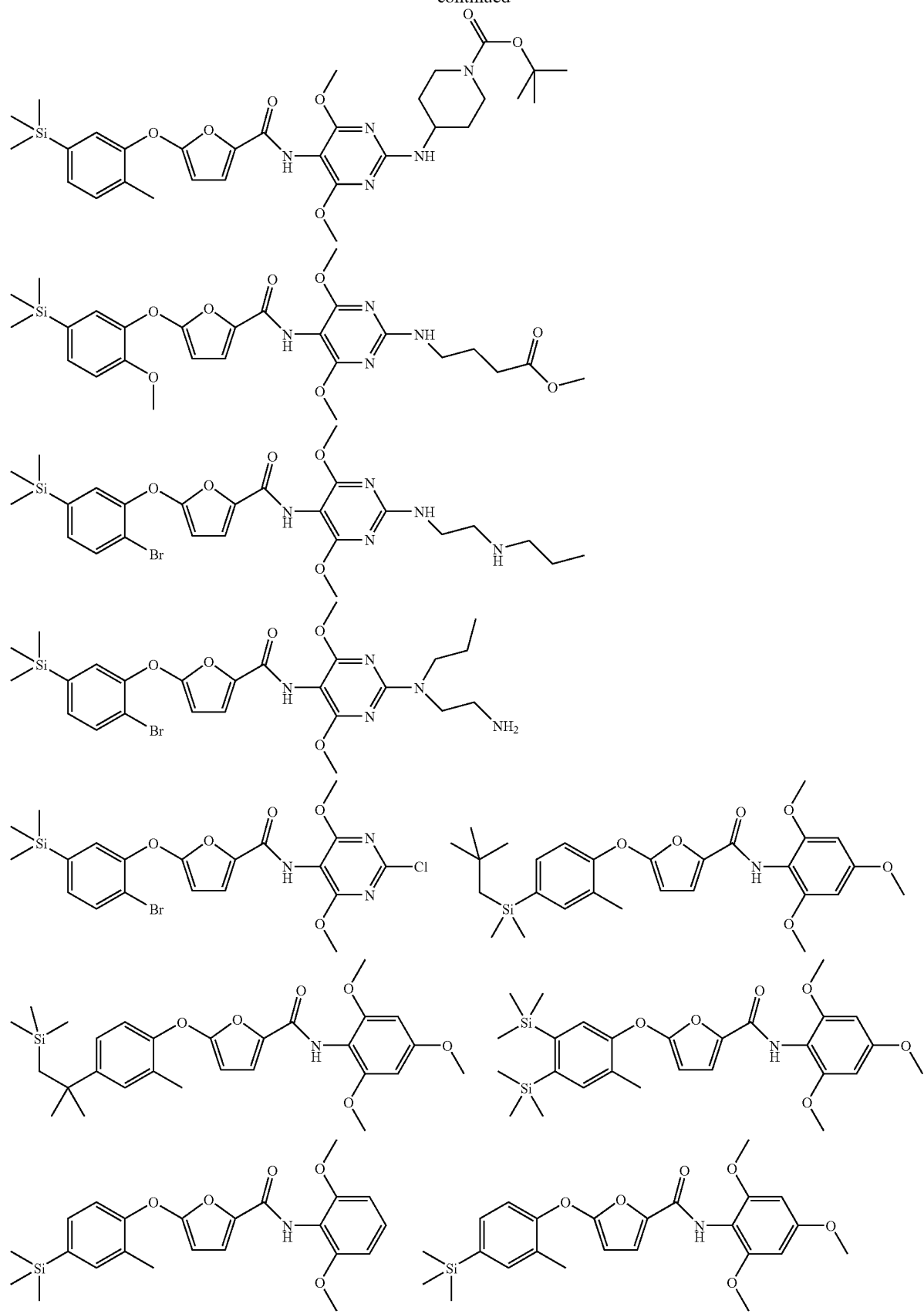

-continued
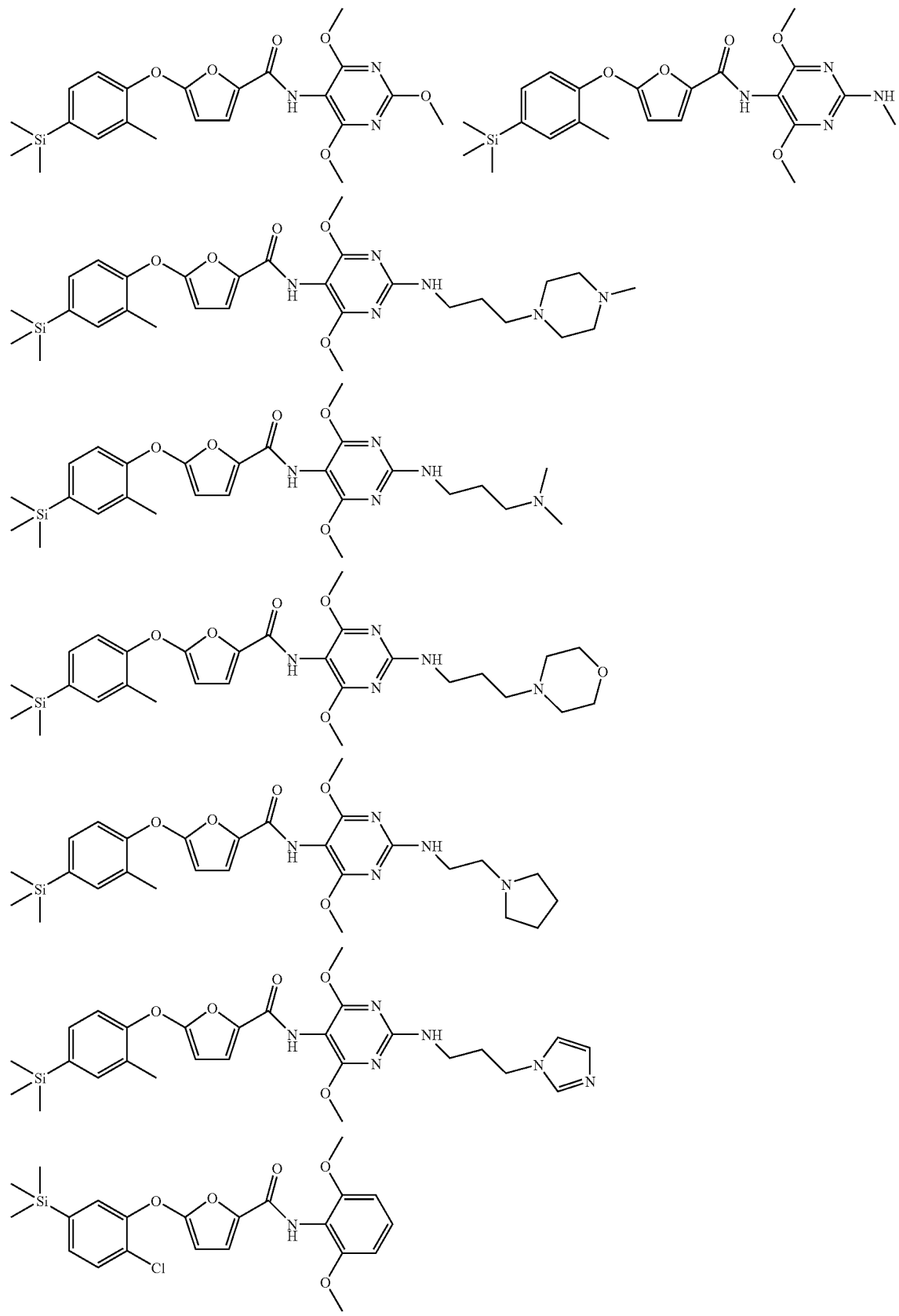

-continued
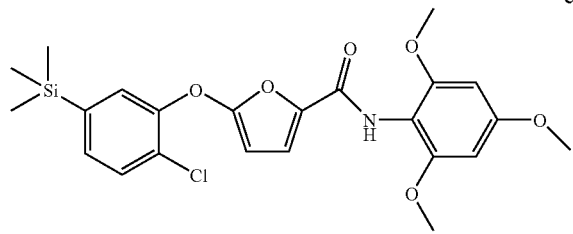
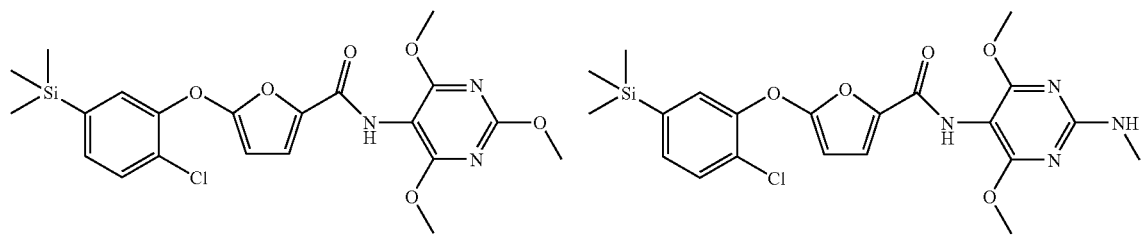
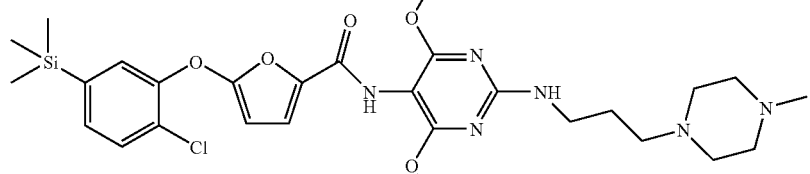
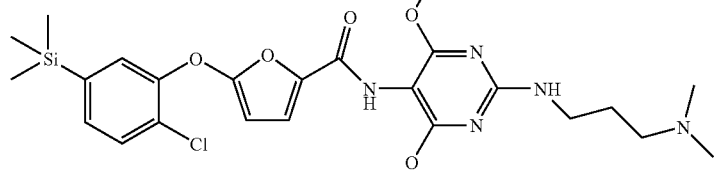
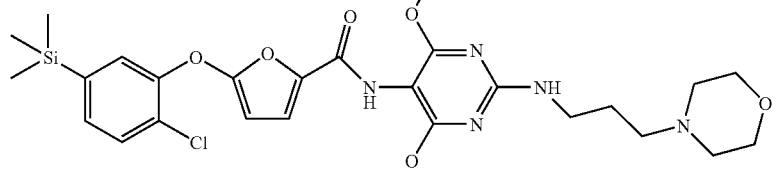
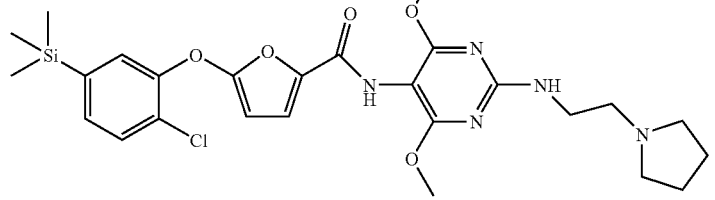
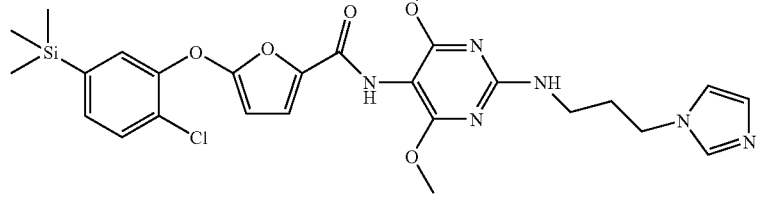

Compounds of the invention may be chiral. They may be in the form of a single enantiomer or diastereomer, or a racemate.

The compounds of the invention may be prepared in racemic form, or prepared in individual enantiomeric form by specific synthesis or resolution as will be appreciated in the art. The compounds may, for example, be resolved into their enantiomers by standard techniques, such as the formation of diastereomeric pairs by salt formation with an optically active acid followed by fractional crystallisation and regeneration of the free base. Alternatively, the enantiomers of the novel compounds may be separated by HPLC using a chiral column.

Some compounds of the formula may exist in different tautomeric forms, which also fall within the scope of the invention.

A compound of the invention may be in a protected amino, or protected hydroxy or protected carboxy form. The terms "protected amino", "protected is hydroxy" and "protected carboxy" as used herein refer to amino, hydroxy and carboxy groups which are protected in a manner familiar to those skilled in the art. For example, an amino group can be protected by a benzyloxycarbonyl, tert-butoxycarbonyl, acetyl or like group, or in the form of a phthalimido or like group. A carboxyl group can be protected in the form of a readily cleavable ester such as the methyl, ethyl, benzyl or tert-butyl ester.

Some compounds of the formula may exist in the form of solvates, for example hydrates, which also fall within the scope of the present invention.

Compounds of the invention may be in the form of pharmaceutically acceptable salts, for example, addition salts of inorganic or organic acids. Such inorganic acid addition salts include, for example, salts of hydrobromic acid, hydrochloric acid, nitric acid, phosphoric acid and sulphuric add. Organic acid addition salts include, for example, salts of acetic acid, benzenesulphonic acid, benzoic acid, camphorsulphonic acid, citric acid, 2-(4-chlorophenoxy)-2-methylpropionic acid, 1,2-ethanedisulphonic acid, ethanesulphonic acid, ethylenediaminetetraacetic acid (EDTA), fumaric acid, glucoheptonic acid, gluconic acid, glutamic acid, N-glycolylarsanilic acid, 4-hexylresorcinol, hippuric acid, 2-(4-hydroxybenzoyl)benzoic acid, 1-hydroxy-2-naphthoic acid, 3-hydroxy-2-naphthoic acid, 2-hydroxyethanesulphonic acid, lactobionic acid, n-dodecyl sulphuric acid, maleic acid, malic acid, mandelic acid, methanesulphonic acid, methyl sulphuric acid, mucic acid, 2-naphthalenesulphonic acid, pamoic acid, pantothenic acid, phosphanilic acid ((4-aminophenyl)phosphonic acid), picric acid, salicylic acid, stearic acid, succinic acid, tannic acid, tartaric acid, terephthalic acid, p-toluenesulphonic acid, 10-undecenoic acid and the like.

It will be appreciated that such salts, provided that they are pharmaceutically acceptable, may be used in therapy. Such salts may be prepared by reacting the compound with a suitable acid in a conventional manner.

A compound of the invention may be prepared by any suitable method known in the art and/or by the following processes:

Scheme 1

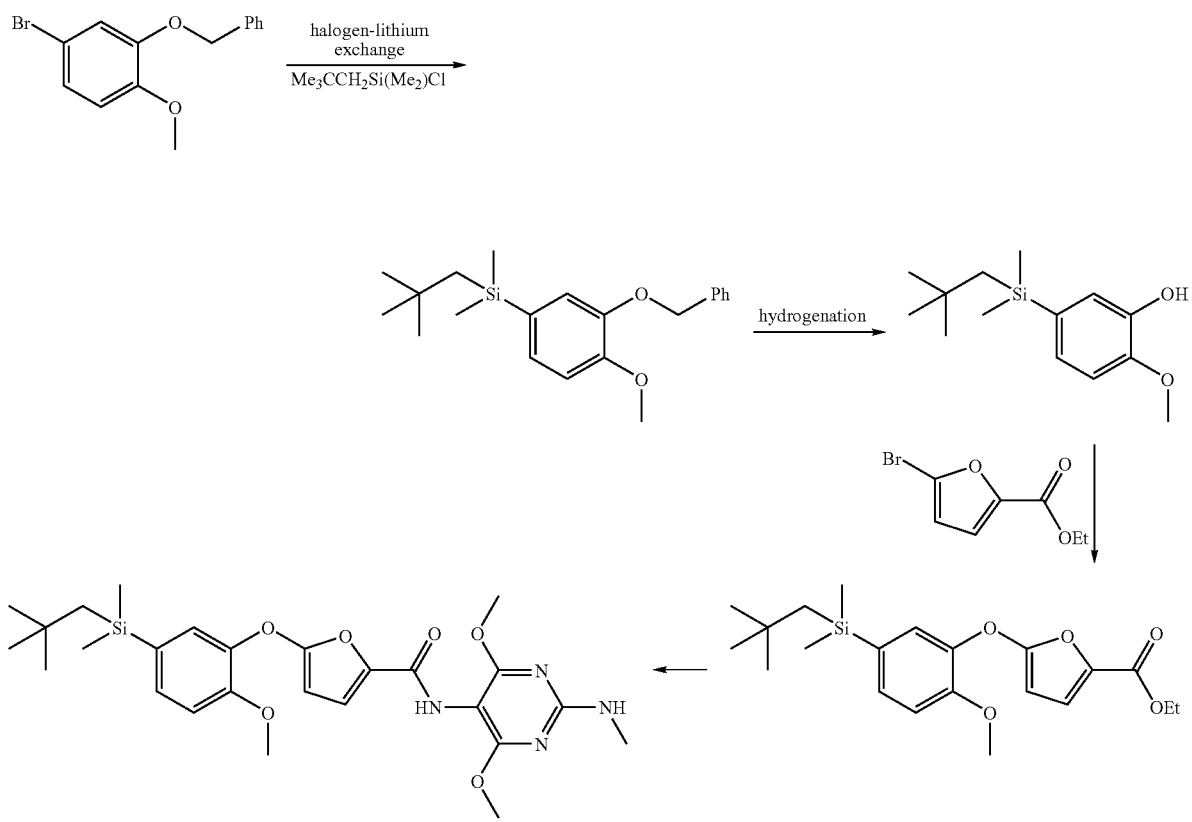

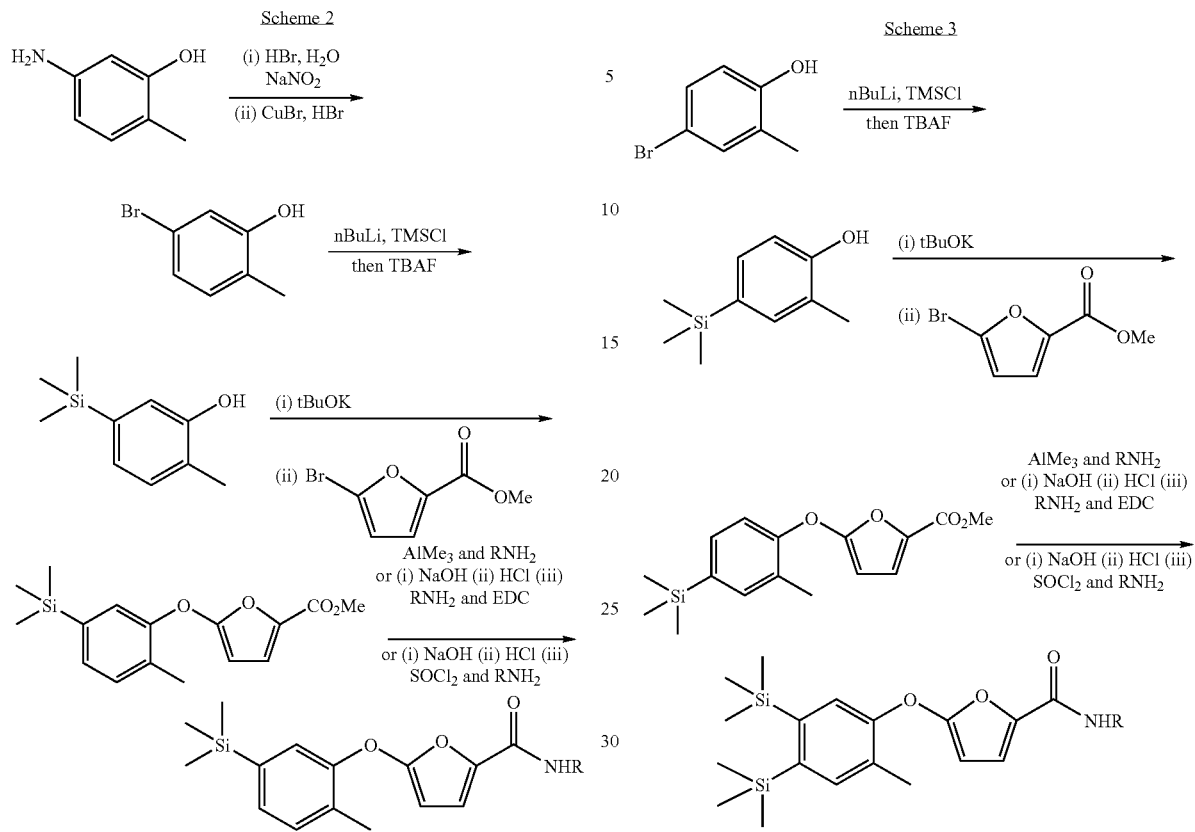
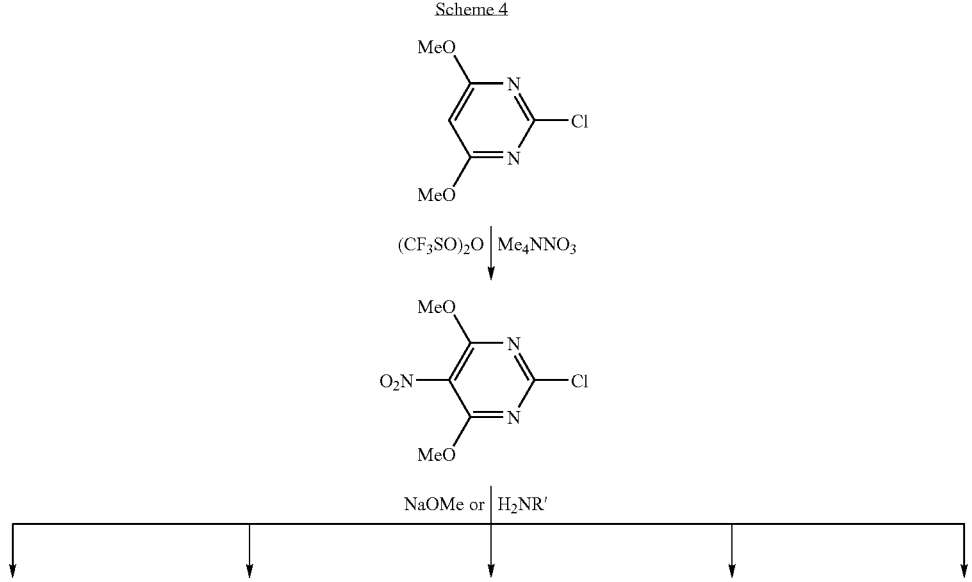

-continued

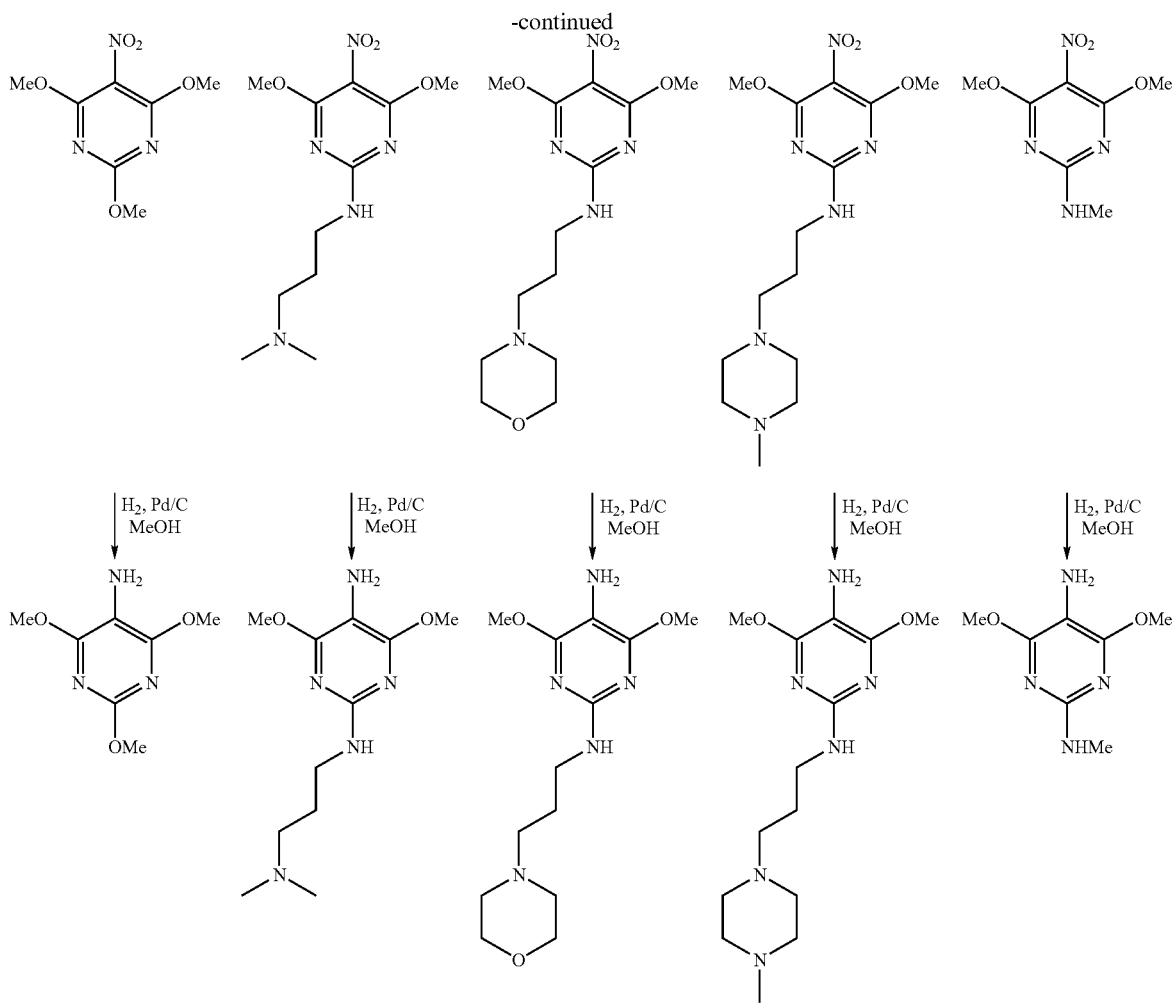

It will be understood that the processes detailed above are solely for the purpose of illustrating the invention and should not be construed as limiting. A process utilising similar or analogous reagents and/or conditions known to one skilled in the art may also be used to obtain a compound of the invention.

Any mixtures of final products or intermediates obtained can be separated on the basis of the physico-chemical differences of the constituents, in a known manner, into the pure final products or intermediates, for example by chromatography, distillation, fractional crystallisation, or by the formation of a salt if appropriate or possible under the circumstances.

The activity and selectivity of the compounds may be determined by any suitable assay known in the art.

The compounds of the invention may be used in the treatment of numerous ailments, conditions and diseases including, but not limited thereto, cancer, endometriosis, uterine myoma, an ovarian disease, a mammary cystic disease, prostatic hypertrophy, amenorrhea, precocious puberty, premenstrual syndrome, a sex-steroid-dependent pathophysiology, benign prostatic hyperplasia, Alzheimer's disease, HIV infection, AIDS and diseases caused by thyroid malfunction, or to arrest spermatogenesis.

The term "cancer" as used herein refers to any disease or condition characterised by uncontrolled, abnormal growth of cells and includes all known types of cancer, for example cancer of the bladder, breast, colon, brain, bone, head, blood, eye, neck, skin, lungs, ovaries, prostate and rectum; digestive, gastrointestinal, endometrial, hematological, AIDS-related, muscoskeletal, neurological and gynecological cancers; lymphomas, melanomas and leukaemia.

In therapeutic use, the active compound may be administered orally, rectally, intra-vaginally, parenterally, by inhalation (pulmonary delivery), topically, ocularly, nasally, or to the buccal cavity. Oral administration is preferred. Thus, the therapeutic compositions of the present invention may take the form of any of the known pharmaceutical compositions for such methods of administration. The compositions may be formulated in a manner known to those skilled in the art so as to give a controlled release, for example rapid release or sustained release, of the compounds of the present invention. Pharmaceutically acceptable carriers suitable for use in such compositions are well known in the art. The compositions of the invention may contain 0.1-99% by weight of active compound. The compositions of the invention are generally prepared in unit dosage form. Preferably, a unit dose comprises the active ingredient in an amount of 1-500 mg. The excipients used in the preparation of these compositions are the excipients known in the art.

Appropriate dosage levels may be determined by any suitable method known to one skilled in the art. It will be understood, however, that the specific dose level for any particular patient will depend upon a variety of factors including the activity of the specific compound employed, the age, body weight, general health, sex, diet, time of administration, route of administration, rate of excretion, drug combination and the severity of the disease undergoing treatment.

Compositions for oral administration are preferred compositions of the invention and there are known pharmaceutical forms for such administration, for example tablets, capsules, granules, syrups and aqueous or oily suspensions. The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions, and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example corn starch or alginic acid; binding agents, for example starch gelatin, acacia, microcrystalline cellulose or polyvinyl pyrrolidone; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long-chain aliphatic alcohols, for example heptadecaethyleneoxycetanol, or condensation products of ethylene oxide with partial esters derived from fatty acids, for example polyoxyethylene sorbitan monooleate. The aqueous suspensions may also contain one or more preservatives, for example ethyl or n-propyl p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavouring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable sweetening, flavouring and colouring agents may also be present.

The pharmaceutical compositions of the invention may also be in the form of oil-in-water emulsions. The oily phase may be a vegetable oil, for example olive oil or arachis oil, or a mineral oil, for example liquid paraffin, or mixtures of these. Suitable emulsifying agents may be naturally occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid, find use in the preparation of injectables.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compositions for topical administration are also suitable for use in the invention. The pharmaceutically active compound may be dispersed in a pharmaceutically acceptable cream, ointment or gel. A suitable cream may be prepared by incorporating the active compound in a topical vehicle such as light liquid paraffin, dispersed in a aqueous medium using surfactants. An ointment may be prepared by mixing the active compound with a topical vehicle such as a mineral oil or wax. A gel may be prepared by mixing the active compound with a topical vehicle comprising a gelling agent. Topically administrable compositions may also comprise a matrix in which the pharmaceutically active compounds of the present invention are dispersed so that the compounds are held in contact with the skin in order to administer the compounds transdermally.

The following Examples illustrate the invention.

In the Examples, all syntheses were carried out under dry nitrogen. Tetrahydrofuran (THF), diethyl ether, dichloromethane, toluene and m-xylene were dried and purified according to standard procedures and stored under nitrogen. Light petroleum refers to the fraction with b. p. 40-60° C.

Thin layer chromatography (TLC) was performed on silica (SiO$_2$) plates. $^1$H NMR spectra were generated at 400 MHz in CDCl$_3$ unless otherwise stated.

Intermediate 1: 5-Bromo-2-methylphenol

To a solution of 5-amino-2-methylphenol (10 g, 81.2 mmol) in hydrobromic acid (40 mL, 48% solution) and water (50 mL) at 0° C. was added a solution of sodium nitrite (5.6 g, 81.2 mmol) in water (15 mL) and the mixture stirred at this temperature for 30 minutes. To this was added copper (I) bromide (11.6 g, 81.2 mmol) in hydrobromic acid (15 mL, 48% solution) and the reaction was subsequently heated at reflux for 2 hours. Upon cooling to room temperature the resulting mixture was extracted with ethyl acetate (2×200 mL) and the combined organic extracts were washed with aqueous potassium hydroxide solution (~1 M, 200 mL), dried (magnesium sulphate) and concentrated under reduced pressure. The crude product was purified by column chromatography [SiO$_2$; light petroleum to 4:1 light petroleum-ethyl acetate] to give the title compound as a colourless oil, which crystallised to give fine colourless needles upon standing overnight (4 g, 26%). R$_f$=0.26 [4:1 light petroleum-ethyl acetate]. $^1$H NMR δ 2.21 (3 H, s), 4.89-4.95 (1 H, br, s), 6.96-6.97 (1 H, br, m), 6.99-7.00 (2 H, m).

Intermediate 2: 2-methyl-5-(trimethylsilyl)phenoxytrimethylsilane

To a solution of 5-bromo-2-methylphenol (Intermediate 1, 3.6 g, 19.3 mmol) in THF (150 mL) at −78° C. was added n-butyl lithium (30 mL, 1.6 M solution in hexanes, 48.1 mmol) and the reaction stirred at this temperature for 30 minutes. Trimethylsilyl chloride (6.1 mL, 48.1 mmol) was then added and the solution stirred at −78° C. for 1.5 hours. The reaction was allowed to warm to room temperature and water (75 mL) was added. The mixture was extracted with diethyl ether (2×75 mL) and the combined organic extracts were dried (magnesium sulphate) and concentrated under reduced pressure to afford 2-methyl-5-(trimethylsilyl)phenoxytrimethylsilane (5 g) as a yellow oil. $^1$H NMR δ$_H$ 0.26 (9 H, s), 0.29 (9 H, s), 2.20 (3 H, s), 6.93 (1 H, d, J=1.1 Hz), 7.04 (1 H, dd, J=7.3, 1.1 Hz), 7.16 (1 H, d, J=7.4 Hz).

Intermediate 3: 5-Trimethylsilyl-2-methylphenol

To a solution of 2-methyl-5-(trimethylsilyl)phenoxytrimethylsilane (Intermediate 2; 5 g) in diethyl ether (40 mL) at room temperature was added tetrabutylammonium fluoride (TBAF; 19.3 mL, 1.0 M solution, 19.3 mmol). The reaction was stirred at this temperature for 5 minutes and then water (40 mL) was added. The mixture was extracted with diethyl ether (2×40 mL) and the combined organic extracts were dried (magnesium sulphate), concentrated under reduced pressure and purified by column chromatography (SiO$_2$; light petroleum to 9:1 light petroleum-diethyl ether) to give the title compound as a colourless oil (1.9 g, 56%). R$_f$=0.32 (9:1 light petroleum-diethyl ether). $^1$H NMR δ$_H$ 0.26 (9 H, s), 2.27 (3 H, s), 4.62 (1 H, s), 6.93 (1 H, d, J=1.0 Hz), 7.02 (1 H, dd, J=7.3, 1.0 Hz), 7.15 (1 H, d, J=7.3 Hz).

Intermediate 4: Methyl 5-[2-methyl-5-(trimethylsilyl)phenoxy]furan-2-carboxylate To a solution of 5-trimethylsilyl-2-methylphenol (Intermediate 3; 653 mg, 3.6 mmol) in THF was added potassium tert-butoxide (407 mg, 3.6 mmol) and the reaction heated at reflux for 1.5 hours. The resulting solution was allowed to cool to room temperature and concentrated under reduced pressure. The residue was taken up in dimethyl sulphoxide (10 mL), treated with methyl 5-bromo-2-furoate (632 mg, 3.1 mmol) and heated at 85° C. for 18 hours. The dark brown mixture was allowed to cool to room temperature, diluted with water (10 mL) and then acidified by the addition of hydrochloric acid (1 M). The mixture was extracted with diethyl ether (3×30 mL) and the combined organic extracts were dried (magnesium sulphate), concentrated under reduced pressure and purified by column chromatography (SiO$_2$; light petroleum to 95:5 light petroleum-diethyl ether) to give the title compound as a colourless oil (534 mg, 57%). R$_f$=0.21 (9:1 light petroleum-diethyl ether). LCMS R$_t$=4.9 mins, m/z=305 (MH$^+$).

Intermediate 5: 5-[2-methyl-5-(trimethylsilyl)phenoxy]furan-2-carboxylic acid

To a solution of methyl 5-[2-methyl-5-(trimethylsilyl)phenoxy]furan-2-carboxylate (Intermediate 4; 217 mg, 0.71 mmol) in methyl alcohol (3 mL) at room temperature was added a solution of sodium hydroxide (126 mg) in water (1 mL) and the reaction stirred for 18 hours. The resulting mixture was concentrated under reduced pressure, the residue taken up in water and extracted into diethyl ether (1×20 mL). The aqueous layer was acidified with hydrochloric acid (1 M) and extracted with ethyl acetate (2×25 mL). The organic extracts were dried (magnesium sulphate) and concentrated under reduced pressure to give the title compound as a colourless powder (181 mg, 87%). R$_f$=0.21 (9:1, dichloromethane-methyl alcohol). LCMS R$_t$=4.33 minutes, m/z=291 (MH$^+$).

The amines required for coupling were commercially available. Alternatively, they can be obtained using the procedures described in WO-A-02/098363, as outlined in Scheme 4 herein.

Intermediate 6: 2-methyl-4-(trimethylsilyl)phenol

To a solution of 4-bromo-2-methylphenol (1.5 g, 8.02 mmol) in THF (16 mL) at −78° C. was added n-butyl lithium (12.5 mL, 1.6 M solution in hexanes, 20.05 mmol) and the reaction was stirred at this temperature for 30 minutes. Trimethylsilyl chloride (2.5 mL, 20.05 mmol) was then added and the resulting mixture was stirred at −78° C. for a further 1.5 hours. The reaction was allowed to warm to room temperature and saturated ammonium chloride solution (10 mL) was added. The mixture was extracted with diethyl ether (2×20 mL) and the combined organic extracts were dried (magnesium sulphate) and concentrated under reduced pressure to give the intermediate 2-methyl-4-(trimethylsilyl)phenoxytrimethylsilane as a pale yellow oil (1.6 g). This intermediate was then diluted with THF (3 mL) and treated with TBAF (6.3 mL, 1.0 M solution in THF, 6.33 mmol) at room temperature. The reaction was stirred at this temperature for 5 minutes and poured into water (10 mL). The aqueous portion was then extracted with ether (3×5 mL) and the combined organic extracts were washed (saturated brine), dried (magnesium sulphate) and concentrated under reduced pressure. The resulting oily residue was pre-adsorbed onto silica and the 2-methyl-4-(trimethylsilyl)phenol isolated by column chromatography (SiO$_2$; light petroleum to 7:3 light petroleum-diethyl ether) as a pale yellow oil (0.78 g, 68%). R$_f$=0.65 (7:3 light petroleum-diethyl ether, silica). $^1$H NMR (DMSO-d$_6$): δ$_H$ 0.17 (9 H, s), 2.1 (3 H, s), 6.77 (1 H, d, J=7.8 Hz), 7.12 (1 H, d, J=7.8 Hz), 7.17 (1 H, s), 9.36 (1 H, s).

General Procedure A

To a suspension of the amine or amine hydrochloride (2 equiv.) in toluene at −30° C. was added trimethylaluminium (2.0 M solution in toluene, 2 to 8 equiv.) dropwise. The reaction was allowed to warm to −20° C. over 30 minutes and then to room temperature over a further 30 minutes. This solution was then added to a solution of methyl 5-[2-methyl-5-(trimethylsilyl)phenoxy]furan-2-carboxylate (Intermediate 4; 1 equiv.) in dichloromethane at 0° C. The mixture was allowed to warm to room temperature and was then further warmed to ~40° C. and stirred until analysis by TLC indicated complete reaction. The reaction was cooled to room temperature and quenched by the dropwise addition of saturated aqueous ammonium acetate. The resultant precipitate was removed by filtration, washing with several portions of ethyl acetate. The filtrate was washed with water and the organic phase was dried (magnesium sulphate), concentrated under reduced pressure and purified to give the required amide.

General Procedure B

To a solution of 5-[2-methyl-5-(trimethylsilyl)phenoxy]furan-2-carboxylic acid (Intermediate 5; 1 equiv.) in N,N-dimethylformamide (DMF; ~5 mL per 1.4 mmol of substrate) was added 1-(3-dimethylaminopropyl)-3-ethylcarbodiimide hydrochloride (EDC.HCl; 2 equiv.), aniline (1 equiv.) and triethylamine (3 equiv.). The reaction was allowed to stir at room temperature until analysis by TLC indicated complete conversion. The solution was concentrated under reduced pressure then taken up in ethyl acetate and washed with hydrochloric acid (1 M solution) then saturated aqueous sodium bicarbonate solution. The organic extracts were dried (magnesium sulphate) and concentrated under reduced pressure and purified to give the required amide.

EXAMPLE 1

5-[2-Methyl-5-(trimethylsilyl)phenoxy]-N-(2,4,6-trimethoxyphenyl)furan-2-carboxamide This compound was prepared according to General Procedure A. $R_f$=0.10 (1:1 light petroleum-ethyl acetate). LCMS $R_t$=4.7 mins, m/z=456 (MH$^+$).

EXAMPLE 2

5-[2-Methyl-5-(trimethylsilyl)phenoxy]-N-(2,4,6-trimethoxy-1,3-pyrimidin-5-yl)furan-2-carboxamide This compound was prepared according to General Procedure A. $R_f$=0.26 (1:1 light petroleum-ethyl acetate). LCMS $R_t$=4.98 minutes, m/z=458 (MH$^+$)

EXAMPLE 3

5-[2-Methyl-5-(trimethylsilyl)phenoxy]-N-(2-methylamino-4,6-dimethoxy-1,3-pyrimidin-5-yl)furan-2-carboxamide This compound was prepared according to General Procedures A and B. $R_f$=0.21 (1:1 light petroleum-ethyl acetate). LCMS $R_t$=4.69 minutes, m/z=457 (MH$^+$).

EXAMPLE 4

5-[2-methyl-5-(trimethylsilyl)phenoxy]-N-{2-[(3-morpholin-4-yl)propylamino]-4,6-dimethoxy-1,3-pyrimidin-5-yl}furan-2-carboxamide This compound was prepared according to General Procedures A and B. $R_f$=0.43 (9:1 dichloromethane-methyl alcohol). LCMS $R_t$=4.59 minutes, m/z=570 (MH$^+$).

EXAMPLE 5

5-[2-methyl-5-(trimethylsilyl)phenoxy]-N-{2-[3-(4-methylpiperazin-1-yl)propylamino]-4,6-dimethoxy-pyrimidin-5-yl}furan-2-carboxamide This compound was prepared according to General Procedures A and B. $R_f$=0.20 (9:1 dichloromethane-methyl alcohol containing 1% 0.880 ammonia solution). LCMS $R_t$=4.61 minutes, m/z=583 (MH$^+$).

EXAMPLE 6

5-[2-methyl-5-(trimethylsilyl)phenoxy]-N-{2-[3-(N,N-dimethylamino)propylamino]-4,6-dimethoxy-1,3-pyrimidin-5-yl}furan-2-carboxamide This compound was prepared according to General Procedure A. $R_f$=0.40 (9:1 dichloromethane-methyl alcohol containing 1% 0.880 ammonia solution). LCMS $R_t$=5.36 minutes, m/z=528 (MH$^+$).

EXAMPLE 7

5-[2-methyl-4-(trimethylsilyl)phenoxy]-N-{2-[3-(morpholin-4-yl)propylamino]-4,6-dimethoxy-1,3-pyrimidin-5-yl}furan-2-carboxamide This compound was prepared according to General Procedures A and B.

What is claimed is:
1. A compound of formula (I) or formula (II)

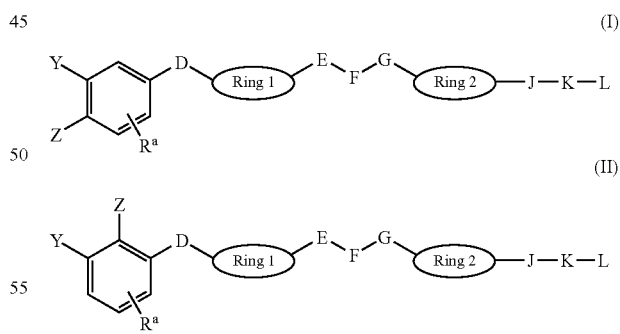

wherein
D is —(CH$_2$)$_n$—, —C(=X)—, —O—, —S(O)$_m$—, —C(=X)N(R$^c$)—, —C(R$^b$)$_2$—, —C(R$^b$)=C(R$^b$)—, —CH(R$^b$)CH(R$^b$)—;
E is optionally present and is —(CH$_2$)$_n$—, —N(R$^d$)—, —(CH$_2$)$_n$N(R$^d$)— or —N(R$^d$)(CH$_2$)$_n$—;
F is —C(=X)— or —N(R$^d$)—;
G is —(CH$_2$)$_n$—, —N(R$^d$)—, —(CH$_2$)$_n$N(R$^d$)— or —N(R$^d$)(CH$_2$)$_n$;

J is optionally present and is —O—, —N(R$^c$)—, —C(=X)N(R$^c$)—, —S(O)$_m$—, —N(R$^c$)S(O)$_m$—, —S(O)$_m$N(R$^c$)— or —N(R$^e$)—;

K is optionally present and is alkylene optionally substituted with R$^b$; or K is cycloalkylene, cycloalkenylene, arylene, heterocycloalkylene, heterocycloalkylene or heteroarylene, any of which is optionally substituted with R$^a$;

L is hydrogen, halogen, —N(R$^f$)$_2$, cycloalkyl, cycloalkenyl, aryl, heterocycloalkyl, heterocycloalkenyl or heteroaryl, any of which is optionally substituted with R$^a$, —C(=X)OR$^d$, —OH, —OR$^c$, —C(=X)N(R$^b$)(R$^c$), —S(O)$_m$N(R$^b$)(R$^C$) or —CN;

each R$^a$ is the same or different and is hydrogen, halogen, alkyl, aryl, hydroxy, alkoxy, -alkoxy-(CH$_2$)$_n$C(O)$_2$R$^b$, —O-aryl, —C(=X)R$^c$, —NO$_2$, —CN, —N(R$^c$)C(=X)R$^c$, —C(=X)N(R$^c$)$_2$, —S(O)$_2$N(R$^c$)$_2$ or —N(R$^e$)$_2$;

each R$^b$ is the same or different and is hydrogen or alkyl;

each R$^c$ is the same or different and is alkyl, cycloalkyl, -alkyl-aryl, -alkyl-cycloalkyl or aryl optionally substituted with R$^a$;

each R$^d$ is the same or different and is hydrogen, alkyl or aryl optionally with R$^a$;

each R$^e$ is the same or different and is hydrogen, alkyl; or R$^e$ is aryl or heteroaryl, either of which is optionally substituted with R$^a$;

each R$^f$ is the same or different and is hydrogen or alkyl; or R$^f$—N—R$^f$ taken together form heterocycloalkyl, heterocycloalkenyl or heteroaryl;

each X is the same or different and is oxygen or sulphur;

Y and Z are the same or different and are each hydrogen, halogen, alkyl, hydroxy, alkoxy, —CN, —N(R$^d$)C(=X)R$^c$, —C(=X)N(R$^c$)(R$^d$), —S(O)$_m$—R$^c$, —N(R$^c$)(R$^d$)S(O)$_2$, —S(O)$_2$N(R$^c$)(R$^d$), —N(R$^e$)$_2$, —Si(R$^c$)$_3$, -alkyl-Si(R$^c$)$_3$, aryl optionally substituted with R$^a$ or —O- aryl optionally substituted with R$^a$;

Rings 1 and 2 are the same or different and are each arylene or heteroarylene, either of which is optionally substituted with R$^a$;

each m is the same or different and is 0, 1 or 2; and each n is the same or different and is 0, 1, 2, or 3;

with the provisos that at least one of Y and Z comprises a silicon atom and that the compound does not comprise a N—N single bond;

or a pharmaceutically acceptable salt thereof.

2. The compound according to claim 1, wherein Y is —Si(R$^c$)$_3$, -alkyl-Si(R$^c$)$_3$ or hydrogen.

3. The compound according to claim 2, wherein each R$^c$ is the same or different and is alkyl.

4. The compound according to claim 1, wherein Z is hydrogen, —Si(R$^c$)$_3$, -alkyl-Si(R$^c$)$_3$, —O-aryl, halogen or alkoxy.

5. The compound to claim 4, wherein each R$^c$ is the same or different and is alkyl or phenyl.

6. The compound according to claim 1, wherein R$^a$ is alkyl, halogen or alkoxy.

7. The compound according to claim 1, wherein D is —O—, —S— or —CH$_2$—.

8. The compound according to claim 1, wherein E is absent.

9. The compound according to claim 1, wherein F is —C(O)—.

10. The compound according to claim 1, wherein G is —N(R$^d$)—.

11. The compound according to claim 10, wherein R$^d$ is hydrogen.

12. The compound according to claim 1, wherein J and K are absent, and L is hydrogen or —N(R$^f$)$_2$.

13. The compound according to claim 1, wherein J is —NH—, K is alkylene and L is heterocycloalkyl.

14. The compound according to claim 1, wherein Ring 1 is heteroarylene.

15. The compound according to claim 14, wherein Ring 1 is furanylene.

16. The compound according to claim 1, wherein Ring 1 is phenylene.

17. The compound according to claim 1, wherein Ring 2 is phenylene, pyrimidylene or pyridinylene, any of which is optionally substituted.

18. The compound according to claim 17, wherein Ring 2 is substituted 1, 2 or 3 times, the substituents being the same or different in each occurrence and selected from alkoxy and halogen.

19. The compound according to claim 1, selected from:

5-[2-methyl-5-(trimethylsilyl)phenoxy]-N-(2,6-dimethoxyphenyl)furan-2-carboxamide;

5-[2-methyl-5-(trimethylsilyl)phenoxy]-N-(2,4,6-trimethoxyphenyl)furan-2-carboxamide;

5-[2-methyl-5-(trimethylsilyl)phenoxy]-N-(2,4,6-trimethoxy-1,3-pyrimidin-5-yl)furan-2-carboxamide;

5-[2-methyl-5-(trimethylsilyl)phenoxy]-N-(2-methylamino-4,6-dimethoxy-1,3-pyrimidin-5-yl)furan-2-carboxamide;

5-[2-methyl-5-(trimethylsilyl)phenoxy]-N-{2-[3-(4-methylpiperazin-1-yl)propylamino]-4,6-dimethoxy-1,3-pyrimidin-5-yl}furan-2-carboxamide;

5-[2-methyl-5-(trimethylsilyl)phenoxy]-N-{2-[3-(N,N-dimethylamino)propylamino]-4,6-dimethoxy-1,3-pyrimidin-5-yl}furan-2-carboxamide;

5-[2-methyl-5-(trimethylsilyl)phenoxy]-N-{2-[3-(morpholin-4-yl)propylamino]-4,6-dimethoxy-1,3-pyrimidin-5-yl}furan-2-carboxamide;

5-[2-methyl-5-(trimethylsilyl)phenoxy]-N-{2-[2-(pyrrolidin-1-yl)ethylamino]-4,6-dimethoxy-1,3-pyrimidin-5-yl}furan-2-carboxamide;

5-[2-methyl-5-(trimethylsilyl)phenoxy]-N-{2-[3-(1,3-imidaz-1-yl)propylamino]-4,6-dimethoxy-1,3-pyrimidin-5-yl}furan-2-carboxamide;

5-[2-bromo-5-(trimethylsilyl)phenoxy]-N-(2,6-dimethoxyphenyl)furan-2-carboxamide;

5-[2-bromo-5-(trimethylsilyl)phenoxy]-N-(2,4,6-trimethoxyphenyl)furan-2-carboxamide;

5-[2-bromo-5-(trimethylsilyl)phenoxy]-N-(2,4,6-trimethoxy-1,3-pyrimidin-5-yl)furan-2-carboxamide;

5-[2-bromo-5-(trimethylsilyl)phenoxy]-N-(2-methylamino-4,6-dimethoxy-1,3-pyrimidin-5-yl)furan-2-carboxamide;

5-[2-bromo-5-(trimethylsilyl)phenoxy]-N-{2-[3-(4-methylpiperazinyl)propylamino]-4,6-dimethoxy-1,3-pyrimidin-5-yl}furan-2-carboxamide;

5-[2-bromo-5-(trimethylsilyl)phenoxy]-N-{2-[3-(N,N-dimethylamino)propylamino]-4,6-dimethoxy-1,3-pyrimidin-5-yl}furan-2-carboxamide;

5-[2-bromo-5-(trimethylsilyl)phenoxy]-N-{2-[3-(morpholin-4-yl)propylamino]-4,6-dimethoxy-1,3-pyrimidin-5-yl}furan-2-carboxamide;

5-[2-bromo-5-(trimethylsilyl)phenoxy]-N-{2-[2-(pyrrolidin-1-yl)ethylamino]-4,6-dimethoxy-1,3-pyrimidin-5-yl}furan-2-carboxamide;

5-[2-bromo-5-(trimethylsilyl)phenoxy]-N-{2-[3-(1,3-imidaz-1-yl)propylamino]-4,6-dimethoxy-1,3-pyrimidin-5-yl}furan-2-carboxamide;

5-[2-methoxy-5-(trimethylsilyl)phenoxy]-N-(2,6-dimethoxyphenyl)furan-2-carboxamide;

5-[2-methoxy-5-(trimethylsilyl)phenoxy]-N-(2,4,6-trimethoxyphenyl)furan-2-carboxamide;
5-[2-methoxy-5-(trimethylsilyl)phenoxy]-N-(2,4,6-trimethoxy-1,3-pyrimidin-5-yl)furan-2-carboxamide;
5-[2-methoxy-5-(trimethylsilyl)phenoxy]-N-(2-methylamino-4,6-dimethoxy-1,3-pyrimidin-5-yl)furan-2-carboxamide;
5-[2-methoxy-5-(trimethylsilyl)phenoxy]-N-{2-[3-(4-methylpiperazin-1-yl)propylamino]-4,6-dimethoxy-1,3-pyrimidin-5-yl}furan-2-carboxamide;
5-[2-methoxy-5-(trimethylsilyl)phenoxy]-N-{2-[3-(N,N-dimethylamino)propylamino]-4,6-dimethoxy-1,3-pyrimidin-5-yl}furan-2-carboxamide;
5-[2-methoxy-5-(trimethylsilyl)phenoxy]-N-{2-[3-(morpholin-4-yl)propylamino]-4,6-dimethoxy-1,3-pyrimidin-5-yl}furan-2-carboxamide;
5-[5-(ethyldimethylsilyl)-2-methylphenoxy]-N-(2,6-dimethoxyphenyl)furan-2-carboxamide;
5-[5-(ethyldimethylsilyl)-2-methylphenoxy]-N-(2,4,6-trimethoxyphenyl)furan-2-carboxamide;
5-[5-(ethyldimethylsilyl)-2-methylphenoxy]-N-(2,4,6-trimethoxy-1,3-pyrimidin-5-yl)furan-2-carboxamide;
5-[5-(ethyldimethylsilyl)-2-methylphenoxy]-N-(2-methylamino-4,6-dimethoxy-1,3-pyrimidin-5-yl)furan-2-carboxamide;
5-[5-(ethyldimethylsilyl)-2-methylphenoxy]-N-{2-[3-(4-methylpiperazin-1-yl)propylamino]-4,6-dimethoxy-1,3-pyrimidin-5-yl}furan-2-carboxamide;
5-[5-(ethyldimethylsilyl)-2-methylphenoxy]-N-{2-[3-(N,N-dimethylamino)propylamino]-4,6-dimethoxy-1,3-pyrimidin-5-yl}furan-2-carboxamide;
5-[5-(ethyldimethylsilyl)-2-methylphenoxy]-N-{2-[3-(morpholin-4-yl)propylamino]-4,6-dimethoxy-1,3-pyrimidin-5-yl}furan-2-carboxamide;
5-{5-[(2,2-dimethylpropyl)dimethylsilyl]-2-methylphenoxy}-N-(2,6-dimethoxyphenyl)furan-2-carboxamide;
5-{5-[(2,2-dimethylpropyl)dimethylsilyl]-2-methylphenoxy}-N-(2,4,6-trimethoxyphenyl)furan-2-carboxamide;
5-{5-[(2,2-dimethylpropyl)dimethylsilyl]-2-methylphenoxy}-N-(2,4,6-trimethoxy-1,3-pyrimidin-5-yl)furan-2-carboxamide;
5-{5-[(2,2-dimethylpropyl)dimethylsilyl]-2-methylphenoxy}-N-(2-methylamino-4,6-dimethoxy-1,3-pyrimidin-5-yl)furan-2-carboxamide;
5-{5-[(2,2-dimethylpropyl)dimethylsilyl]-2-methylphenoxy}-N-{2-[3-(4-methylpiperazin-1-yl)propylamino]-4,6-dimethoxy-1,3-pyrimidin-5-yl}furan-2-carboxamide;
5-{5-[(2,2-dimethylpropyl)dimethylsilyl]-2-methylphenoxy}-N-{2-[3-(N,N-dimethylamino)propylamino]-4,6-dimethoxy-1,3-pyrimidin-5-yl}furan-2-carboxamide;
5-{5-[(2,2-dimethylpropyl)dimethylsilyl]-2-methylphenoxy}-N-{2-[3-(morpholin-4-yl)propylamino]-4,6-dimethoxy-1,3-pyrimidin-5-yl}furan-2-carboxamide;
5-{5-[1,1-dimethyl-2-(trimethylsilyl)ethyl]-2-methylphenoxy}-N-(2,6-dimethoxyphenyl)furan-2-carboxamide;
5-{5-[1,1-dimethyl-2-(trimethylsilyl)ethyl]-2-methylphenoxy}-N-(2,4,6-trimethoxyphenyl)furan-2-carboxamide;
5-{5-[1,1-dimethyl-2-(trimethylsilyl)ethyl]-2-methylphenoxy}-N-(2,4,6-trimethoxy-1,3-pyrimidin-5-yl)furan-2-carboxamide;
5-{5-[1,1-dimethyl-2-(trimethylsilyl)ethyl]-2-methylphenoxy}-N-(2-methylamino-4,6-dimethoxy-1,3-pyrimidin-5-yl)furan-2-carboxamide;
5-{5-[1,1-dimethyl-2-(trimethylsilyl)ethyl]-2-methylphenoxy}-N-{2-[3-(4-methylpiperazin-1-yl)propylamino]-4,6-dimethoxy-1,3-pyrimidin-5-yl}furan-2-carboxamide;
5-{5-[1,1-dimethyl-2-(trimethylsilyl)ethyl]-2-methylphenoxy}-N-{2-[3-(N,N-dimethylamino)propylamino]-4,6-dimethoxy-1,3-pyrimidin-5-yl }furan-2-carboxamide;
5-{5-[1,1-dimethyl-2-(trimethylsilyl)ethyl]-2-methylphenoxy}-N-{2-[3-(morpholin-4-yl)propylamino]-4,6-dimethoxy-1,3-pyrimidin-5-yl}furan-2-carboxamide;
5-{[2-methyl-5-(trimethylsilyl)phenyl]methyl}-N-(2,6-dimethoxyphenyl)furan-2-carboxamide;
5-{[2-methyl-5-(trimethylsilyl)phenyl]methyl}-N-(2,4,6-trimethoxyphenyl)furan-2-carboxamide;
5-{[2-methyl-5-(trimethylsilyl)phenyl]methyl}-N-(2,4,6-trimethoxy-1,3-pyrimidin-5-yl)furan-2-carboxamide;
5-{[2-methyl-5-(trimethylsilyl)phenyl]methyl}-N-(2-methylamino-4,6-dimethoxy-1,3-pyrimidin-5-yl)furan-2-carboxamide;
5-{[2-methyl-5-(trimethylsilyl)phenyl]methyl}-N-{2-[3-(4-methylpiperazin-1-yl)propylamino]-4,6-dimethoxy-1,3-pyrimidin-5-yl}furan-2-carboxamide;
5-{[2-methyl-5-(trimethylsilyl)phenyl]methyl-N-{2-[3-(N,N-dimethylamino)propylamino]-4,6-dimethoxy-1,3-pyrimidin-5-yl}furan-2-carboxamide;
5-{[2-methyl-5-(trimethylsilyl)phenyl]methyl}-N-{2-[3-(morpholin-4-yl)propylamino]-4,6-dimethoxy-1,3-pyrimidin-5-yl}furan-2-carboxamide;
5-[2-methoxy-4-phenoxy-5-(trimethylsilyl)phenylthio]-N-[4,6-dimethoxy-(2-phenylamino)-1,3-pyrimidin-5-yl]furan-2-carboxamide;
5-{2-methoxy-5-[(2,2-dimethylpropyl)dimethylsilyl]phenoxy}-N-[2-(N-tert-butyloxycarbonylpiperidinyl-4'-amino)-4,6-dimethoxy-1,3-pyrimidin-5-yl]furan-2-carboxamide;
5-{2-methoxy-5-[(2,2-dimethylpropyl)dimethylsilyl]phenoxy}-N-{2-[3-(1,3-imidaz-1-yl)propylamino]-4,6-dimethoxy-1,3-pyrimidin-5-yl}furan-2-carboxamide;
5-{[(1,1-dimethylethyl)dimethylsilyl]phenoxy}-N-(2,4,6-trimethoxyphenyl)benzene-3-carboxamide;
5-[2-methoxy-4-(dimethylphenylsilyl)phenoxy]-N-{2-[2-(ethylamino)ethylamino]-4,6-dimethoxy-1,3-pyrimidin-5-yl}furan-2-carboxamide;
5-[4-chloro-2-methyl-5-(trimethylsilyl)phenoxy]-N-(2,4,6-trimethoxy-1,3-pyrimidin-5-yl}furan-2-carboxamide;
5-[4-chloro-2-methoxy-6-methyl-3-(trimethylsilyl)phenoxy]-N-{2-[3-(4-methylpiperazin-1-yl)propylamino]-4,6-dimethoxy-1,3-pyrimidin-5-yl}furan-2-carboxamide;
5-[2-methyl-5-(propyldimethylsilyl)phenoxy]-N-(2,4,6-trimethoxyphenyl)furan-2-carboxamide;
5-[2-methyl-5-(trimethylsilyl)phenoxy]-N-[2-(N-tert-butyloxycarbonylpiperidinyl-4'-amino)-4,6-dimethoxy-1,3-pyrimidin-5-yl]furan-2-carboxamide;
5-[2-methoxy-5-(trimethylsilyl)phenoxy]-N-[2-(3-methoxycarbonylpropylamino)-4,6-dimethoxy-1,3-pyrimidin-5-yl]furan-2-carboxamide;
5-[2-bromo-5-(trimethylsilyl)phenoxy]-N-{[2-(2-(propylamino)ethylamino)]-4,6-dimethoxy-1,3-pyrimidin-5-yl}furan-2-carboxamide;
5-[2-bromo-5-(trimethylsilyl)phenoxy]-N-{2-[(2-aminoethyl)propylamino)]-4,6-dimethoxy-1,3-pyrimidin-5-yl}furan-2-carboxamide;
5-[2-bromo-5-(trimethylsilyl)phenoxy]-N-(2-chloro-4,6-dimethoxy-1,3-pyrimidin-5-yl)furan-2-carboxamide;

5-{2-methyl-4-[(2,2-dimethylpropyl)dimethylsilyl]phenoxy}-N-(2,4,6-trimethoxyphenyl)furan-2-carboxamide;

5-{2-methyl-4-[1,1-dimethyl-2-(trimethylsilyl)ethyl]phenoxy}-N-(2,4,6-trimethoxyphenyl)furan-2-carboxamide;

5-[2-methyl-4,5-bis(trimethylsilyl)phenoxy]-N-(2,4,6-trimethoxyphenyl)furan-2-carboxamide;

5-[2-methyl-4-(trimethylsilyl)phenoxy]-N-(2,6-dimethoxyphenyl)furan-2-carboxamide;

5-[2-methyl-4-(trimethylsilyl)phenoxy]-N-(2,4,6-trimethoxyphenyl)furan-2-carboxamide;

5-[2-methyl-4-(trimethylsilyl)phenoxy]-N-(2,4,6-trimethoxy-1,3-pyrimidin-5-yl)furan-2-carboxamide;

5-[2-methyl-4-(trimethylsilyl)phenoxy]-N-(2-methylamino-4,6-dimethoxy-1,3-pyrimidin-5-yl)furan-2-carboxamide;

5-[2-methyl-4-(trimethylsilyl)phenoxy]-N-{2-[3-(4-methylpiperazin-1-yl)propylamino]-4,6-dimethoxy-1,3-pyrimidin-5-yl}furan-2-carboxamide;

5-[2-methyl-4-(trimethylsilyl)phenoxy]-N-{2-[3-(N,N-dimethylamino)propylamino]-4,6-dimethoxy-1,3-pyrimidin-5-yl}furan-2-carboxamide;

5-[2-methyl-4-(trimethylsilyl)phenoxy]-N-{2-[3-(morpholin-4-yl)propylamino]-4,6-dimethoxy-1,3-pyrimidin-5-yl}furan-2-carboxamide;

5-[2-methyl-4-(trimethylsilyl)phenoxy]-N-{2-[2-(pyrrolidin-1-yl)ethylamino]-4,6-dimethoxy-1,3-pyrimidin-5-yl}furan-2-carboxamide;

5-[2-methyl-4-(trimethylsilyl)phenoxy]-N-{2-[3-(1,3-imidaz-1-yl)propylamino]-4,6-dimethoxy-1,3-pyrimidin-5-yl}furan-2-carboxamide;

5-[2-chloro-5-(trimethylsilyl)phenoxy]-N-(2,6-dimethoxyphenyl)furan-2-carboxamide;

5-[2-chloro-5-(trimethylsilyl)phenoxy]-N-(2,4,6-trimethoxyphenyl)furan-2-carboxamide;

5-[2-chloro-5-(trimethylsilyl)phenoxy]-N-(2,4,6-trimethoxy-1,3-pyrimidin-5-yl)furan-2-carboxamide;

5-[2-chloro-5-(trimethylsilyl)phenoxy]-N-(2-methylamino-4,6-dimethoxy-1,3-pyrimidin-5-yl)furan-2-carboxamide;

5-[2-chloro-5-(trimethylsilyl)phenoxy]-N-{2-[3-(4-methylpiperazin-1-yl)propylamino]-4,6-dimethoxy-1,3-pyrimidin-5-yl}furan-2-carboxamide;

5-[2-chloro-5-(trimethylsilyl)phenoxy]-N-{2-[3-(N,N-dimethylamino)propylamino]-4,6-dimethoxy-1,3-pyrimidin-5-yl}furan-2-carboxamide;

5-[2-chloro-5-(trimethylsilyl)phenoxy]-N-{2-[3-(morpholin-4-yl)propylamino]-4,6-dimethoxy-1,3-pyrimidin-5-yl}furan-2-carboxamide;

5-[2-chloro-5-(trimethylsilyl)phenoxy]-N-{2-[2-(pyrrolidin-1-yl)ethylamino]-4,6-dimethoxy-1,3-pyrimidin-5-yl}furan-2-carboxamide; and 5-[2-chloro-5-(trimethylsilyl)phenoxy]-N-{2-[3-(1,3-imidaz-1-yl)propylamino]-4,6-dimethoxy-1,3-pyrimidin-5-yl}furan-2-carboxamide.

20. The compound according to claim 1, which is in the form of a single enantiomer or diastereomer or tautomer.

21. A pharmaceutical composition comprising a compound of formula (I) or formula (II)

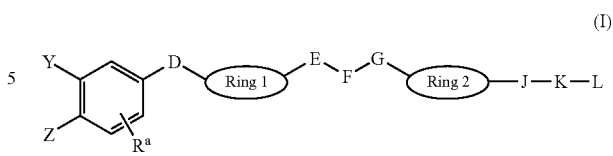

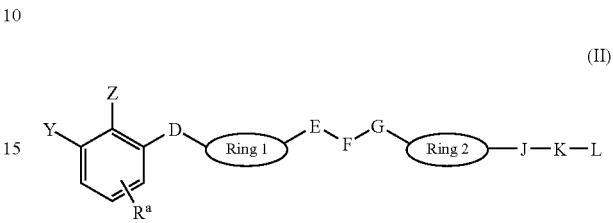

wherein

D is —$(CH_2)_n$—, —C(=X)—, —O—, —S(O)$_m$—, —C(=X)N(R$^e$)—, —C(R$^b$)$_2$—, —C(R$^b$)=C(R$^b$)—, —CH(R$^b$)CH(R$^b$)—;

E is optionally present and is —$(CH_2)_n$—, —N(R$^d$)—, —$(CH_2)_n$N(R$^d$)— or —N(R$^d$)(CH$_2$)$_n$—;

F is —C(=X)— or —N(R$^d$)—;

G is —$(CH_2)_n$—, —N(R$^d$)—, —(CH$_2$)$_n$N(R$^d$)— or —N(R$^d$)(CH$_2$)$_n$;

J is optionally present and is —O—, —N(R$^c$)C(=X)—, —C(=X)N(R$^c$)—, —S(O)$_m$—, —N(R$^c$)S(O)$_m$—, —S(O)$_m$N(R$^c$)— or —N(R$^e$)—;

K is optionally present and is alkylene optionally substituted with R$^b$; or K is cycloalkylene, cycloalkenylene, arylene, heterocycloalkylene, heterocycloalkylene or heteroarylene, any of which is optionally substituted with R$^a$;

L is hydrogen, halogen, —N(R$^f$)$_2$, cycloalkyl, cycloalkenyl, aryl, heterocycloalkyl, heterocycloalkenyl or heteroaryl, any of which is optionally substituted with R$^a$, —C(=X)OR$^d$, —OH, —OR$^c$, —C(=X)N(R$^b$)(R$^c$), —S(O)$_m$N(R$^b$)(R$^c$) or —CN;

each R$^a$ is the same or different and is hydrogen, halogen, alkyl, aryl, hydroxy, alkoxy, -alkoxy-(CH$_2$)$_n$C(O)$_2$R$^b$, —O-aryl, —C(=X)R$^c$, —NO$_2$, —CN, —N(R$^c$)C(=X)R$^c$, —C(=X)N(R$^c$)$_2$, —S(O)$_2$N(R$^c$)$_2$ or —N(R$^e$)$_2$;

each R$^b$ is the same or different and is hydrogen or alkyl;

each R$^c$ is the same or different and is alkyl, cycloalkyl, -alkyl-aryl, -alkyl-cycloalkyl or aryl optionally substituted with R$^a$;

each R$^d$ is the same or different and is hydrogen, alkyl or aryl optionally with R$^a$;

each R$^e$ is the same or different and is hydrogen, alkyl; or R$^e$ is aryl or heteroaryl, either of which is optionally substituted with R$^a$;

each R$^f$ is the same or different and is hydrogen or alkyl, or R$^f$—N—R$^f$ taken together form heterocycloalkyl, heterocycloalkenyl or heteroaryl;

each X is the same or different and is oxygen or sulphur;

Y and Z are the same or different and are each hydrogen, halogen, alkyl, hydroxy, alkoxy, —CN, —N($R^d$)C(=X)$R^c$, —C(=X)N($R^c$)($R^d$), —S(O)$_m$—$R^c$, —N($R^c$)($R^d$)S(O)$_2$, —S(O)$_2$N($R^c$)($R^d$), —N($R^c$)$_2$, —Si($R^c$)$_3$, -alkyl-Si($R^c$)$_3$, aryl optionally substituted with $R^a$ or —O-aryl optionally substituted with $R^a$;

Rings 1 and 2 are the same or different and are each arylene or heteroarylene, either of which is optionally substituted with $R^a$;

each m is the same or different and is 0, 1 or 2; and each n is the same or different and is 0, 1, 2, or 3;

with the provisos that at least one of Y and Z comprises a silicon atom and that the compound does not comprise a N—N single bond;

or a pharmaceutically acceptable salt thereof;

and a pharmaceutically acceptable diluent or carrier.

* * * * *